US009046463B1

(12) United States Patent
Adler et al.

(10) Patent No.: US 9,046,463 B1
(45) Date of Patent: Jun. 2, 2015

(54) METHOD FOR CONDUCTING NONLINEAR ELECTROCHEMICAL IMPEDANCE SPECTROSCOPY

(75) Inventors: Stuart B. Adler, Seattle, WA (US); Jamie R. Wilson, Seattle, WA (US); Shawn L. Huff, Seattle, WA (US); Daniel T. Schwartz, Seattle, WA (US)

(73) Assignee: University of Washington, Seattle, WA (US)

( * ) Notice: Subject to any disclaimer, the term of this patent is extended or adjusted under 35 U.S.C. 154(b) by 1821 days.

(21) Appl. No.: 11/408,594

(22) Filed: Apr. 21, 2006

(51) Int. Cl.
*G01N 27/02* (2006.01)

(52) U.S. Cl.
CPC .............. *G01N 27/02* (2013.01); *G01N 27/021* (2013.01); *G01N 27/028* (2013.01)

(58) Field of Classification Search
CPC .... G01N 27/02; G01N 27/021; G01N 27/028
See application file for complete search history.

(56) References Cited

PUBLICATIONS

Darowicki, Corrosion Science, Corrosion Rate Measurement by Non-linear Electrochemical Impedance Spectroscopy, 1995, p. 913-925.*

Medina, J.A., and D.T. Schwartz, "Nonlinear Dynamics of Limiting Current in The Flow-Modulated Uniform-Injection Cell," *J Electrochem. Soc.* 144(1):155-164, Jan. 1997.

Wilson, J.R., et al., "Full-Spectrum Nonlinear Response of a Sinusoidally Modulated Rotating Disk Electrode," *Physics of Fluids* 17(6):063601-1-063601-11, 2005.

Wilson, J.R., et al., "Nonlinear Electrochemical Impedance Spectroscopy for SOFC Cathode Materials," *Proceedings of the 6th International Symposium on Electrochemical Impedance Spectroscopy*, Cocoa Beach, Florida, May 17, 2004, 21 pages.

Wilson, J.R., et al., "Nonlinear Electrochemical Impedance Spectroscopy for Solid Oxide Fuel Cell Cathode Materials," Electrochimica Acta 51(8-9):1389-1402, Jan. 20, 2006 [available online Aug. 22, 2005].

\* cited by examiner

*Primary Examiner* — Alexander Noguerola
(74) *Attorney, Agent, or Firm* — Christensen O'Connor Johnson Kindness PLLC

(57) ABSTRACT

A method for conducting nonlinear electrochemical impedance spectroscopy. The method includes quantifying the nonlinear response of an electrochemical system by measuring higher-order current or voltage harmonics generated by moderate-amplitude sinusoidal current or voltage perturbations. The method involves acquisition of the response signal followed by time apodization and fast Fourier transformation of the data into the frequency domain, where the magnitude and phase of each harmonic signal can be readily quantified. The method can be implemented on a computer as a software program.

17 Claims, 27 Drawing Sheets

METHOD FOR CONDUCTING NONLINEAR ELECTROCHEMICAL IMPEDANCE SPECTROSCOPY

GOVERNMENT LICENSE RIGHTS

Research leading to the present invention was supported, at least in part, under National Science Foundation Grant No. CTS 0412076, and Department of Energy Grant No. DE-FC26-02NT41566.

BACKGROUND

An electrochemical system is a system in which a chemical change is accompanied by the passage of an electric current. Electrochemical systems occur in nature or can be man made. An example of a naturally occurring electrochemical system is seen whenever galvanic corrosion occurs, such as when two dissimilar metals are in contact with one another through an electrolyte. A common man-made electrochemical system is a dry or a wet cell battery or a fuel cell. Of the many chemical and physical processes taking place within electrochemical systems, kinetic and diffusion processes are important to characterize since these processes are determinative of the extent to which the electrochemical process proceeds at an acceptable rate. It is desirable to understand the rate-limiting processes taking place in such systems to provide better engineering design or materials of construction to improve the system's performance. Methods have been devised to understand such processes. Electrochemical impedance spectroscopy (EIS) is one tool for analyzing an electrochemical system. In EIS, an alternating electric signal of current or voltage is applied to the electrochemical system. The alternating signal produces a frequency-dependent response of current and voltage from the system. These signals are used to calculate the impedance (Z) of the electrochemical system. In order for EIS to be of any use, the response data collected must be associated with an important aspect of the system under consideration. Analyzing responses from electrochemical systems via EIS is a complex process. Computers provide opportunities for enhancing the analysis by performing faster and more complex algorithms to improve the EIS method. To date, EIS testing equipment uses an approximation by assuming the electrochemical processes, are linear. Using a linear approach, while suitable for some systems, may not be appropriate for others. Furthermore, the linear approach may describe very little of the actual processes taking place within the electrochemical system. Accordingly, improvements are continually being sought to the linear EIS approach.

SUMMARY

In view of the aforementioned shortcomings of the prior art, one embodiment of the present invention provides a method for conducting nonlinear electrochemical impedance spectroscopy (NLEIS). The method includes quantifying the nonlinear response of an electrochemical system by measuring higher-order voltage harmonics generated by moderate-amplitude sinusoidal current or voltage perturbations. The method involves acquisition of the response signal, followed by time apodization and transformation of the data into the frequency domain, where the magnitude and phase of each harmonic signal can be readily quantified. In one aspect of the invention, the method can be implemented on a computer as a software program.

In another aspect of the invention, the method can be provided as a computer-readable medium that can provide computer-executable instructions for performing the steps of the method.

In another aspect of the invention, a method can be performed for determining the behavior of an electrochemical system, including, but not limited to fuel cells, fuel cell materials, and batteries for determining rate-limiting processes; coated or noncoated metal components for corrosion testing; animal or plant tissue and organs for determining biomedical behavior, or of semiconducting or any mixed-conducting materials to determine their fundamental electrochemical characteristics.

NLEIS, according to one embodiment, may better isolate the nonlinearities of specific physical processes. NLEIS offers the possibility of first isolating the interface via timescale (at frequencies too high to perturb the interfacial concentration) and then probing its nonlinear response via the perturbation amplitude, while the exchange current density remains constant. In this way, NLEIS may provide a more straightforward pathway to desired nonlinear information, requiring less a priori understanding about other physical processes.

NLEIS, according to one embodiment, may offer improved measurement resolution of nonlinear behavior. Nonlinearities in some systems are very small ($10^{-2}$ or less relative to the dominant linear response). NLEIS confines small nonlinearities of interest to specific frequency bands where they can be distinguished accurately versus noise using Fourier analysis. NLEIS also has the possibility of probing "local" nonlinearities as a function of polarization, for example, as the mechanism changes from one potential range to another.

NLEIS, according to one embodiment, may gather nonlinear information more efficiently. NLEIS, according to one embodiment, can simultaneously acquire second, third, fourth, etc., harmonics that constitute a regular perturbation expansion of the relevant nonlinearity.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
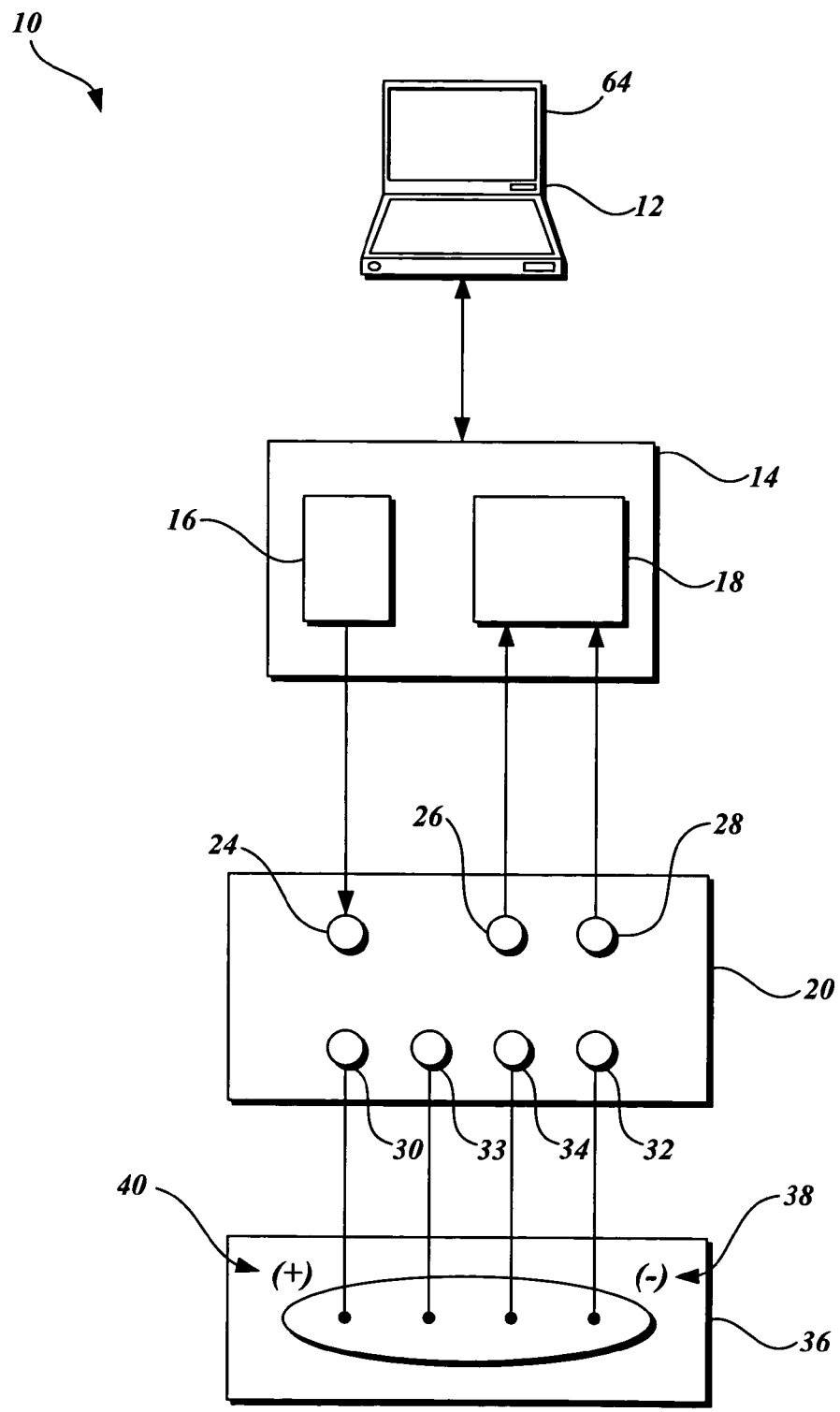
FIG. 1 is a schematic illustration of a system for conducting nonlinear electrochemical impedance spectroscopy in accordance with one embodiment of the present invention.

FIG. 1 is a schematic illustration of a system 10 for conducting nonlinear electrochemical impedance spectroscopy (NLEIS) according to one embodiment of the present invention. The NLEIS system 10 includes, at least, a computer 12, a function generator 16, a digitizer 18, and a potentiostat 20. Not all the components of the NLEIS system 10 are being illustrated for brevity. Furthermore, the NLEIS system 10 depicted in FIG. 1 merely represents one embodiment for the purpose of describing one particular configuration. The description of a single representative embodiment should not be construed to limit the invention to any one particular configuration. The system 10 can be used to probe for potential (voltage) or current harmonic responses of the first harmonic and higher-order harmonics, and contribution of higher-order harmonics for an electrochemical system 36. The electrochemical system 36 can represent any naturally occurring or manmade system in which a chemical change is accompanied by an electric current. Examples of the electrochemical system 36 include a fuel cell, a material or combination of materials used in fuel cells such as an electrolyte or catalyst material, a coated metal workpiece, a battery, and living plant or animal tissue. The probing of living tissue is commonly referred to as a biomedical electrochemical system. The computer 12 may be any stand alone or integrated computer capable of executing instructions via a processor for carrying out a method, as will be discussed in further detail below. The computer 12 includes one or more software modules that perform steps for conducting nonlinear electrochemical impedance spectroscopy. The function generator 16 receives its instructions from computer 12. The function generator 16 generates an alternating sinusoidal signal having a predetermined perturbation amplitude and a predetermined perturbation frequency. The computer 12 may include a software module for calculating a suitable signal having the predetermined amplitude and predetermined frequency. The perturbation signal may be varied across a range in both perturbation amplitude and perturbation frequency. The perturbation signal may cycle through various frequencies at a single perturbation amplitude. The perturbation signal may also be cycled through a range of perturbation amplitudes. According to the present invention, the preferred range of perturbation amplitudes is determined for an electrochemical system. Conducting testing in the preferred range of perturbation amplitudes assures that the response signals obtained from the electrochemical system 36 are representative of processes occurring in the electrochemical system 36. In one embodiment, the preferred range of perturbation amplitudes is the range proportional to a characteristic value of the system. More specifically, the preferred range is that range of sampling for which a mathematical fit of the response signal values to the perturbation signal values raised to the power of the same order is substantially linear.

The perturbation signal generated by function generator 16 passes through a shunt resistor to convert the voltage signal produced by the function generator into an equivalent current if the measurement is being performed galvanostatically (i.e., sending current perturbations). The shunt resistor is a component within the potentiostat 20. It is used to convert current to voltage and vice-versa. For instance, the digitizer 18 can record voltages; thus, the current that the potentiostat 20 reads from the electrochemical system 36 is then passed through the shunt resistor and the resulting voltage (which is proportional to the current via the shunt resistor) is then fed to the digitizer 18. Analogously, the waveform function generator 16 can produce a voltage signal. In order to perturb the system with a current signal, the potentiostat can use the shunt resistor to convert this signal to a current. A potentiostat, such as potentiostat 20, is a device that controls the voltage difference between a working electrode and a reference electrode of the electrochemical system 36. Electrochemical system 36 has a cathode 40 and an anode 38, a working electrode 32, a counter electrode 30, and a first 33 and a second 34 reference electrode. The working electrode 32 is in contact with the point on the electrochemical system 36 where the voltage response of the electrochemical system 36 is measured. The reference electrode 34 is in contact with the point on the electrochemical system 36 used to measure the voltage at the working electrode 32. The counter electrode 30 is in contact with the point on the electrochemical system 36 to complete a circuit. The second reference electrode is placed with the working electrode, to operate together as a working electrode. Current flows from the counter electrode 30 to the working electrode 32. The potential (voltage) is measured/controlled across the two reference electrodes 33, 34. The electrodes 30, 32, 33, and 34 are in contact with one another through an electrolyte or other conductive medium. The potentiostat 20 includes contact point 26 for carrying the voltage response signal from the electrochemical system 36 to the digitizer 18. The potentiostat 20 includes contact point 28 for carrying the current response signal from the electrochemical system 36 to the digitizer 18 via the shunt resistor. The digitizer 18 converts the analog voltage signals representing the current and voltage from the electrochemical system 36 via the potentiostat 20 into digital signals that can be processed by computer 12.

Figure 2:
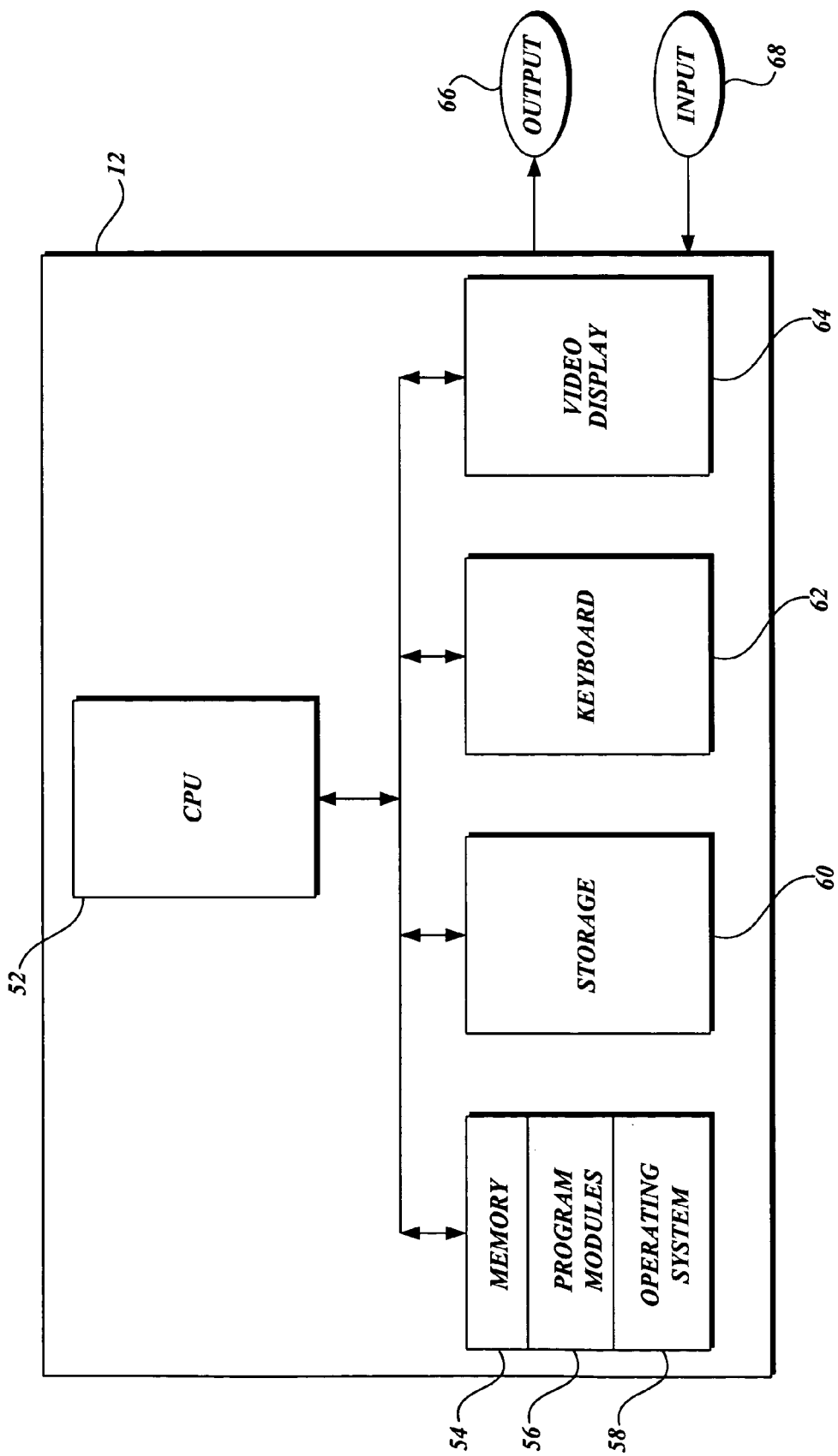
FIG. 2 is a schematic illustration of a computer for conducting nonlinear electrochemical impedance spectroscopy in accordance with one embodiment of the present invention.

Referring to FIG. 2, the computer 12 includes a central processing unit (CPU) 52; a computer-readable medium 54, or memory, containing program software modules 56 for a method of conducting nonlinear electrochemical impedance spectroscopy, an operating system module 58; storage 60; a keyboard 62 and/or a mouse or other input device to provide a user a means of inputting commands, and a video display 64 to provide a means of displaying items. The computer 12 contains software and hardware that allows the computer 12 to issue commands in the form of electrical signals via port 66 and to receive signals via port 68 to process such signals according to the program modules 56. By way of example, and not limitation, computer-readable medium 54 includes computer storage media and communication media. Computer storage media may include volatile and non-volatile, removable and non-removable media implemented in any method or technology for storage of information such as computer-readable instructions, data structures, program modules, or other data. Computer-readable storage media includes, but is not limited to, RAM, ROM, EEPROM, flash memory, or other memory technology, CD-ROM, digital versatile disks (digital videodisc) (DVD) or other optical storage, magnetic cassettes, magnetic tape, magnetic disk storage or other magnetic storage devices, or any other medium which can be used to store information. Communication media typically embodies computer-readable instructions, data structures, program modules or other data in a modulated data signal such as a carrier wave or other transport mechanism and includes any information delivery media. Other aspects of the computer 12 may include network connections to other computers.

It should be understood that FIG. 2 illustrates a representative example of a suitable operating environment in which embodiments of the invention may be implemented. Other computing systems that may be suitable to implement the invention include, but are not limited to personal computers, server computers, hand-held devices or laptop devices, multiprocessor systems, microprocessor-based systems, programmable consumer electronics, minicomputers, mainframe computers, and distributed computing environments.

One embodiment of the present invention may be described in the general context of computer-executable instructions, such as program modules. Generally, program modules include routines, programs, objects, components, and data structures that perform particular tasks or implement particular abstract data types. Modules stored in memory 54 of the computer 12 include modules for conducting nonlinear electrochemical impedance spectroscopy, modules for processing data obtained as a result of applying perturbation signals to an electrochemical system, and modules for comparing amplitude-independent harmonic structures to known patterns.

Figure 3:
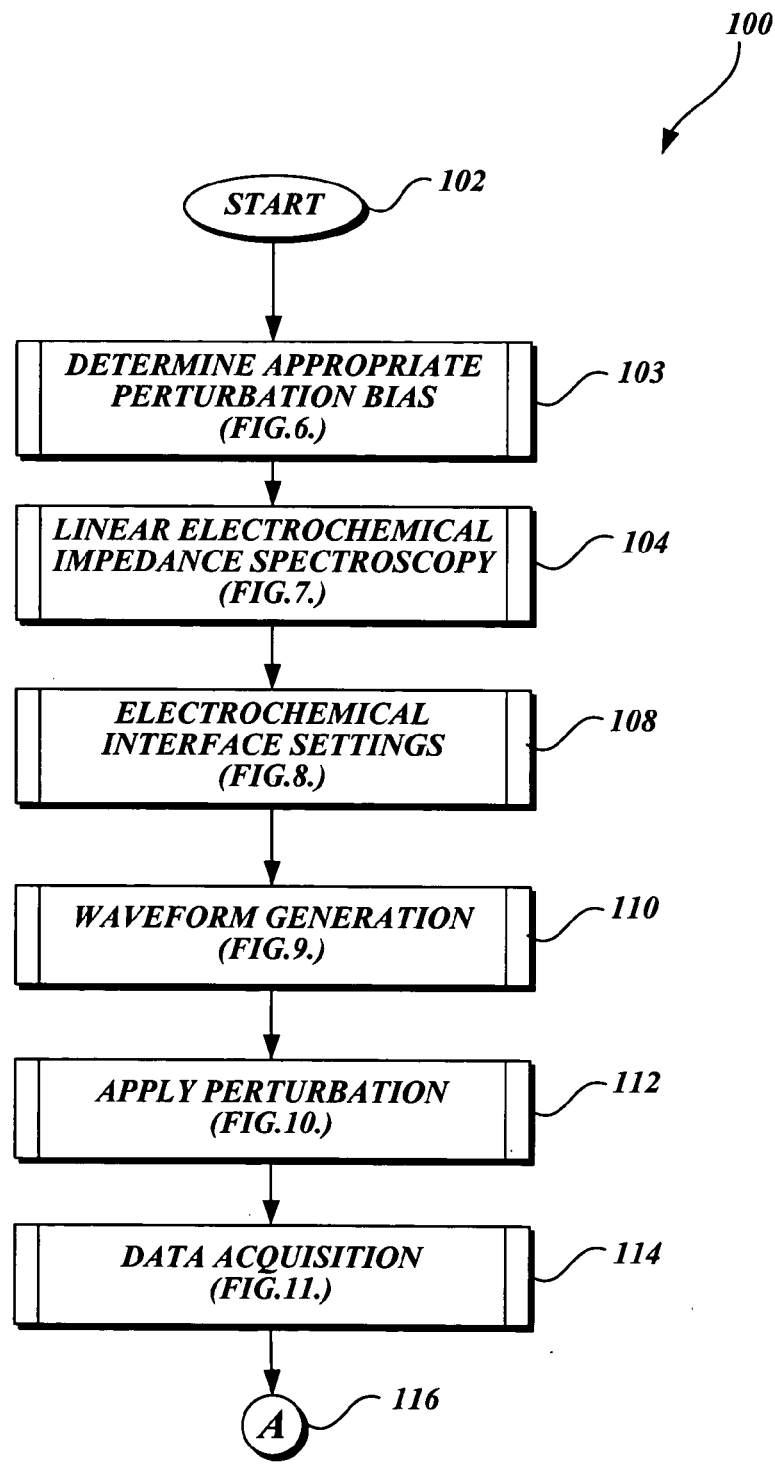
FIG. 3 is a flow diagram of a method for conducting nonlinear electrochemical impedance spectroscopy in accordance with one embodiment of the present invention.

Referring to FIG. 3, a flow diagram of a method 100 for conducting nonlinear electrochemical impedance spectroscopy, according to one embodiment of the present invention, is illustrated. Method 100 begins at start block 102. From start block 102, the method 100 enters block 103. Block 103 is for determining an appropriate perturbation bias. Block 103 is described in more detail in association with FIG. 6. From block 103, the method 100 enters block 104. In block 104, the method 100 performs linear electrochemical impedance spectroscopy. Linear electrochemical impedance spectroscopy applies a small alternating current or voltage to the electrochemical system 36, so as to produce a linear response from the electrochemical system 36. Linear electrochemical impedance spectroscopy is performed initially to obtain an estimate of the amplitudes and frequencies to use in nonlinear electrochemical impedance spectroscopy. While linear EIS relies on small amplitudes, NLEIS as described herein will use perturbations of moderate amplitude, which is further described below. The purpose for conducting perturbation signals of moderate amplitude is to obtain a response signal showing harmonics of orders greater than one. While NLEIS works with harmonics of orders greater than one, EIS does not. Block 104 will be described in further detail in association with FIG. 7. From block 104, the method 100 enters block 108. Block 108 is for determining the electrochemical interface settings. For example, the electrochemical interface settings include adding any biases, attenuating the input and output signals to maximize signal-to-noise ratio, and choosing an appropriate shunt resistor. Block 108 is further described in association with FIG. 8. From block 108, the method 100 enters block 110. Block 110 is for generating the alternating perturbation signal. An alternating perturbation signal will have a waveform with a predetermined perturbation amplitude and a perturbation frequency. The perturbation signal is applied for at least one complete cycle. Block 110 is described in further detail in association with FIG. 9. From block 110, the method 100 enters block 112. Block 112 is for applying the perturbation signal to the electrochemical system 36. Block 112 is described in further detail in association with FIG. 10. From block 112, the method 100 enters block 114. Block 114 is for data acquisition. Data acquisition refers to receiving, collecting, and measuring the current and voltage response signals produced by the electrochemical system 36 in response to the perturbation signal. Block 114 is described in further detail in association with FIG. 11. From block 114, the method 100 enters continuation block 116. Continuation block 116 signifies that method 100 is continued in FIG. 4 starting from continuation block 118. Blocks 103-114 define a method for generating a perturbation signal and obtaining a response signal from the electrochemical system 36.

Figure 4:
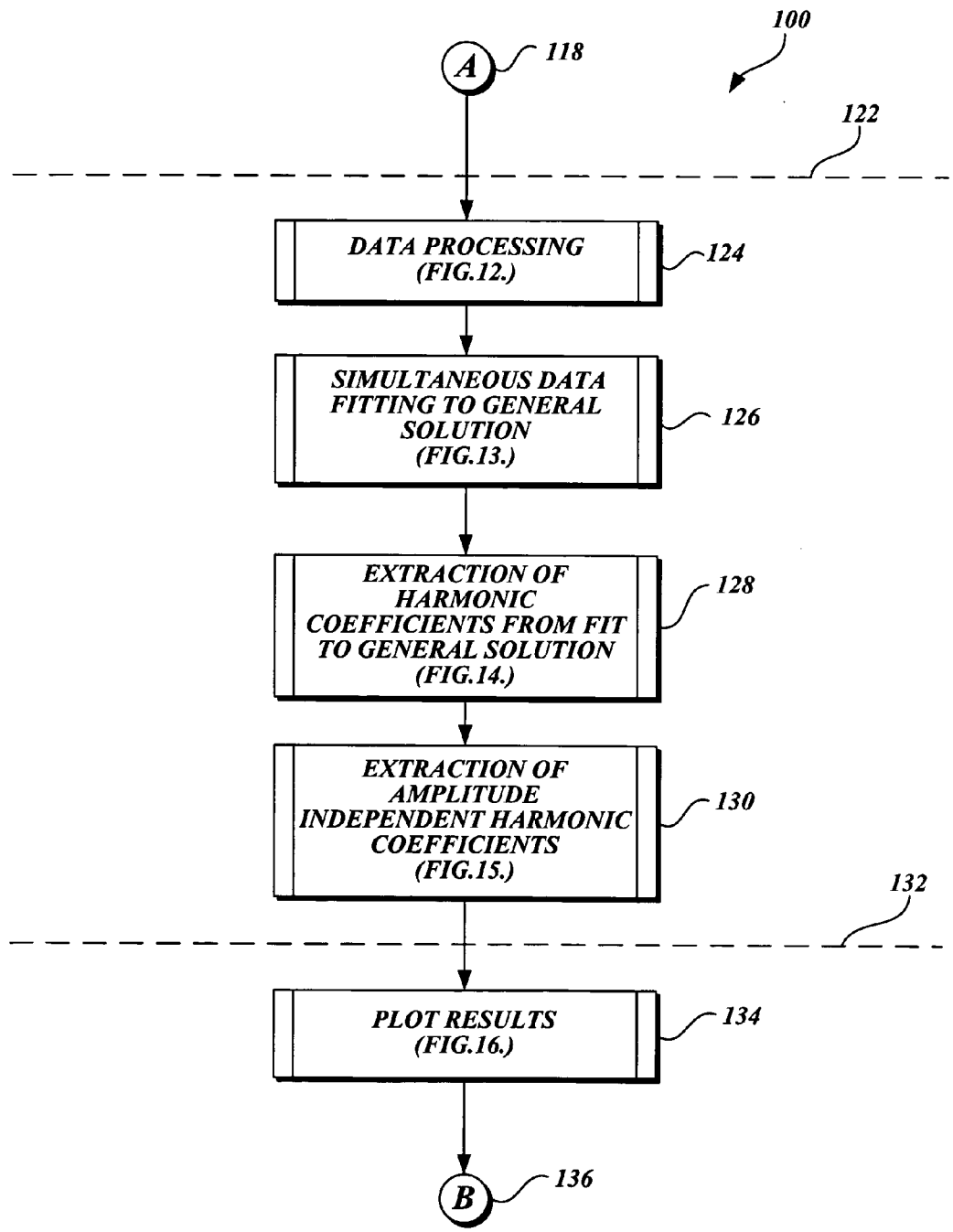
FIG. 4 is a flow diagram of a method for conducting nonlinear electrochemical impedance spectroscopy in accordance with one embodiment of the present invention.

Referring to FIG. 4, from continuation block 118, the method 100 enters block 124.

Figure 19:
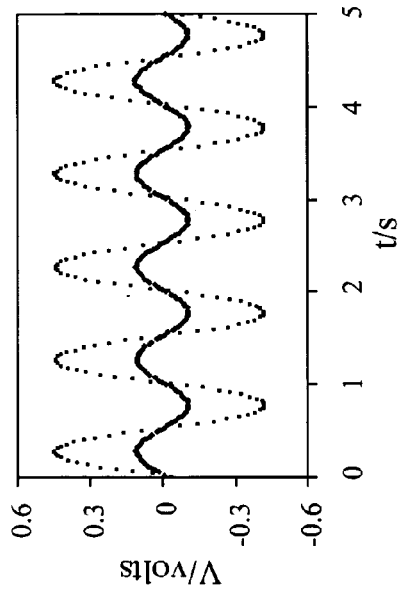
FIG. 19 is a representative plot of the measured perturbation current applied to a LSC-82/SDC/LSC-82 cell at 750° C. in air, at a frequency of 1.0 cycles/second (Hz) as a function of time at perturbation amplitudes of 30 mA and 200 mA.
Figure 20:
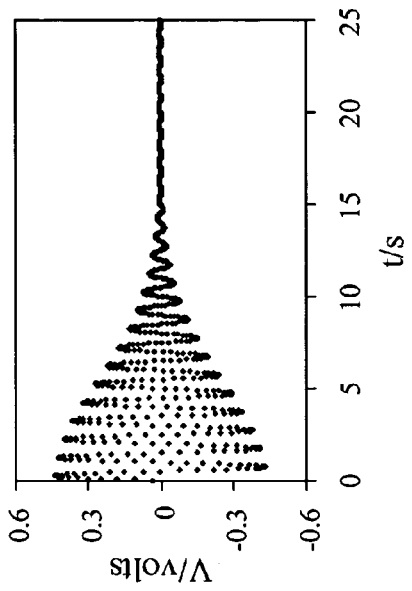
FIG. 20 is a representative plot of the response potential (voltage) as a result of applying the current perturbation described in FIG. 19.

The set of blocks 124-130 defines a method for processing the response signal to derive a harmonic structure showing the contributions of harmonics greater than one. From block 120, the method 100 enters block 124. Block 124 is for processing the data. Data processing in block 120 refers to converting raw voltage data received from the electrochemical system 36 into transformed data using a transform technique, such as fast Fourier transform. The transform technique converts time domain data into frequency domain data. Raw data from the electrochemical system includes current and voltage values as a function of time. When plotted in the time domain, such data appears as a sinusoidal waveform of a certain amplitude and frequency. A representative plot of such data is illustrated in FIGS. 19 and 20. FIGS. 19 and 20 show current and voltage plots, respectively, for two values of perturbation amplitude at a single perturbation frequency. Many sets of data for different perturbation amplitudes and at different perturbation frequencies are collected. By combining multiple sets of voltage data produced at different perturbation amplitudes and at different perturbation frequencies, harmonic patterns can be recognized in the data that occur at certain frequencies. Mathematical calculations are used to define the behavior of one or more of these patterns. "Harmonic structure" or simply "harmonic" in the singular or plural form is used throughout this application to define such behavior in any of its mathematical representations. Block 124 is described in further detail in association with FIG. 12. From block 124, the method 100 enters block 126. Block 126 is for simultaneously fitting the data obtained from block 124 to a general solution. A general solution is a generic representation of the harmonic structure. In this application, a general solution is represented by a linear superposition of steady-periodic harmonics of unknown amplitude and phase (Equation 2a). This equation is then time-apodized and transformed so that it can be compared to the experimental data in the same form to determine the values of the harmonics. Block 126 is described in further detail in association with FIG. 13. From block 126, the method 100 enters block 128. Block 128 is for the extraction of harmonic coefficients from the fit to the general solution. Each harmonic coefficient represents a segment of the overall harmonic structure. Block 128 is described in further detail in association with FIG. 14. From block 128, the method 100 enters block 130. Block 130 is for the extraction of amplitude-independent harmonic coefficients. Amplitude-independent harmonic coefficients can be obtained from the amplitude-dependent harmonic coefficients at a specific frequency via Equation (2e) below. The $\hat{V}_{k,m}(\omega)$ terms are amplitude-independent, while the $\hat{V}_k(\tilde{\imath}, \omega)$ terms are amplitude dependent. Block 130 is described in further detail in association with FIG. 15. As described above, blocks 124-130 describe a set of steps for processing the response signal from the electrochemical system 36 to arrive at the amplitude-independent harmonic structure. When the amplitude-dependent harmonic structure or structures of higher-order harmonics greater than one derived over a range of sampling are plotted as a function of a characteristic value raised to the same power as the order of the harmonic structure of the electrochemical system 36, such as characteristic current or characteristic voltage, is substantially linear, then the perturbation amplitudes of such range of sampling is said to be of moderate amplitude, signifying such data produced over such range of sampling is valid.

From block 130, the method 100 enters block 134.

Figure 5:
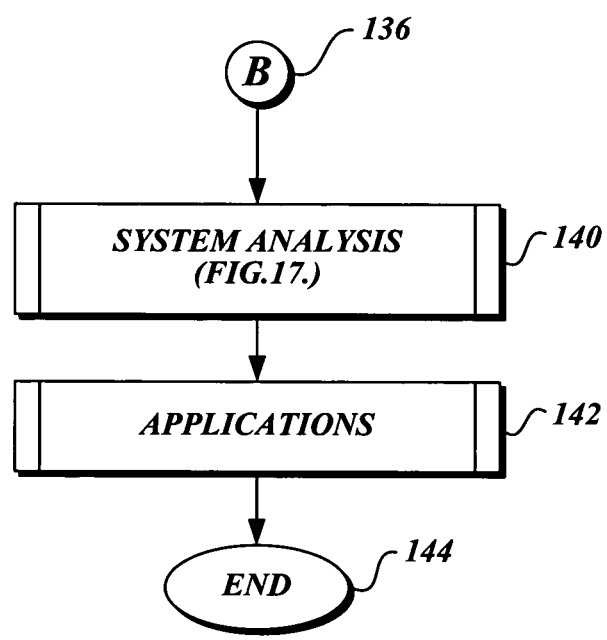
FIG. 5 is a flow diagram of a method for conducting nonlinear electrochemical impedance spectroscopy in accordance with one embodiment of the present invention.

Blocks 134-142 illustrate uses for generating harmonic structures using moderate amplitude perturbations. Block 134 is for plotting results. Block 134 is optional, and may be used to identify which of several known patterns corresponds most closely with the harmonic structure of the electrochemical system under consideration. Block 134 is described in more detail in association with FIG. 16. From block 134, the method 100 enters block 136. Block 136 is a continuation block signifying the continuation of method 100 on block 138 of FIG. 5. Referring to FIG. 5, from block 138, the method 100 enters block 140. Block 140 is for performing analysis of the electrochemical system. Block 140 is described in further detail in association with FIG. 17. From block 140, the method 100 enters block 142. Block 142 is for applying the analysis of block 140 to a particular application, for example, the method 100 may be applied to determine characteristics of a fuel cell, a battery, a metal coating or material, or for a biomedical application. From block 142, the method enters termination block 144. Block 144 indicates the termination of one iteration of method 100.

Figure 6:
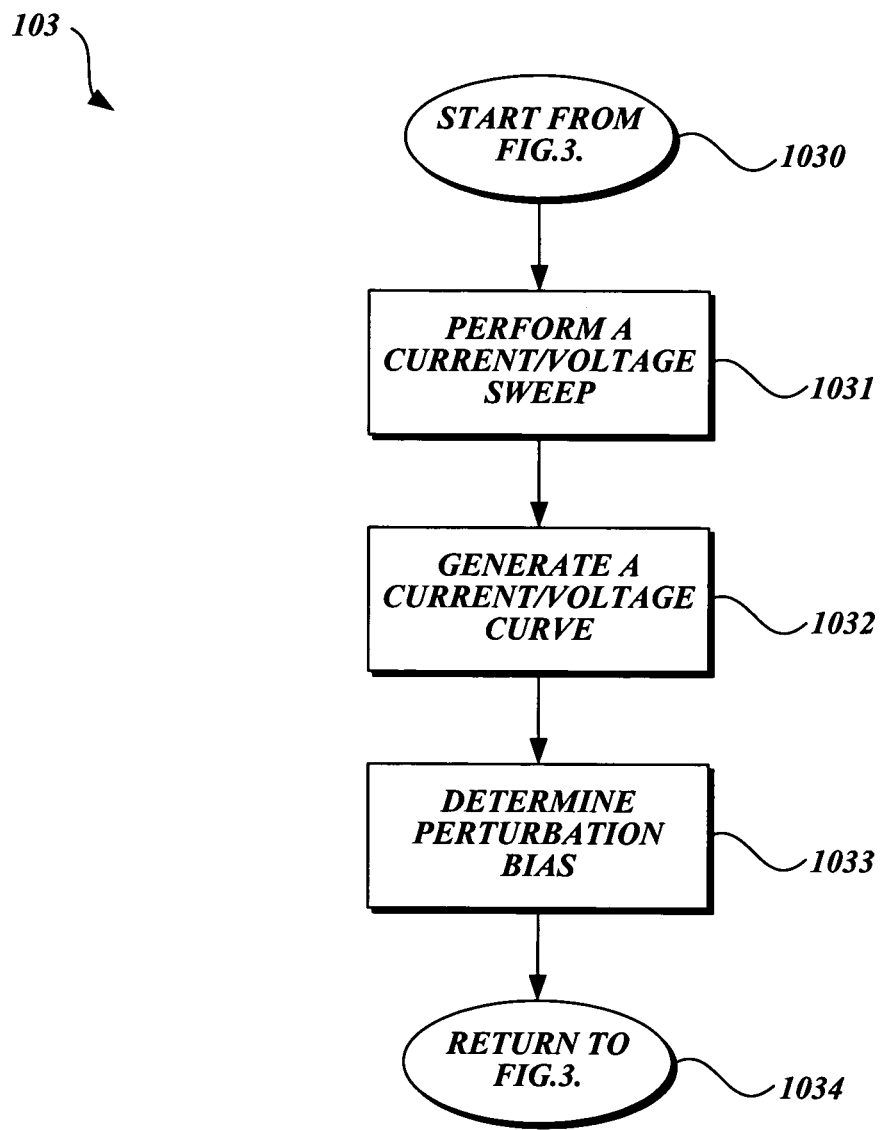
FIG. 6 is a flow diagram of a method for conducting nonlinear electrochemical impedance spectroscopy in accordance with one embodiment of the present invention.

FIG. 6 is a flow diagram of a sub-method 103 used for determining an appropriate perturbation bias. A perturbation bias is a DC "non-alternating" signal that is added to the alternating perturbation to produce a total perturbation that is not symmetric around a current or voltage of zero. Sub-method 103 begins at start block 1030, which is entered from block 103 of FIG. 3. From start block 1030, the sub-method 103 enters block 1031. Block 1031 is for performing a current/voltage sweep. A current/voltage sweep includes applying an increasing (or decreasing) amount of current to the electrochemical system 36 to elicit a voltage response signal from the system 36. A current/voltage sweep includes sweeping across a range of bias. The current is plotted versus voltage. This plot can be useful to help determine if a specific bias should be applied in order to operate in a specific regime. In this application, the examples are operated at zero-bias, but it is possible to operate with an applied bias. The applied bias can be chosen after running a current/voltage sweep. The waveforms of the current and voltage do not need to be centered around zero, unless that is desired. However, in other instances it may be useful to apply a bias. From block 1031, the sub-method 103 enters block 1032. Block 1032 is for generating a current/voltage curve. The current/voltage curve is a plot of the measured perturbation current as a function of voltage or a plot of the measured voltage response signal as a function of current. From block 1032, the sub-method 103 enters block 1033. Block 1033 is for determining a perturbation bias. The bias is chosen by determining in which region of the current/voltage sweep to center the AC perturbation. This can be zero, positive, or negative values. From block 1033, the sub-method 103 enters return block 1034. Block 1034 returns to the method 100 of FIG. 3.

Figure 7:
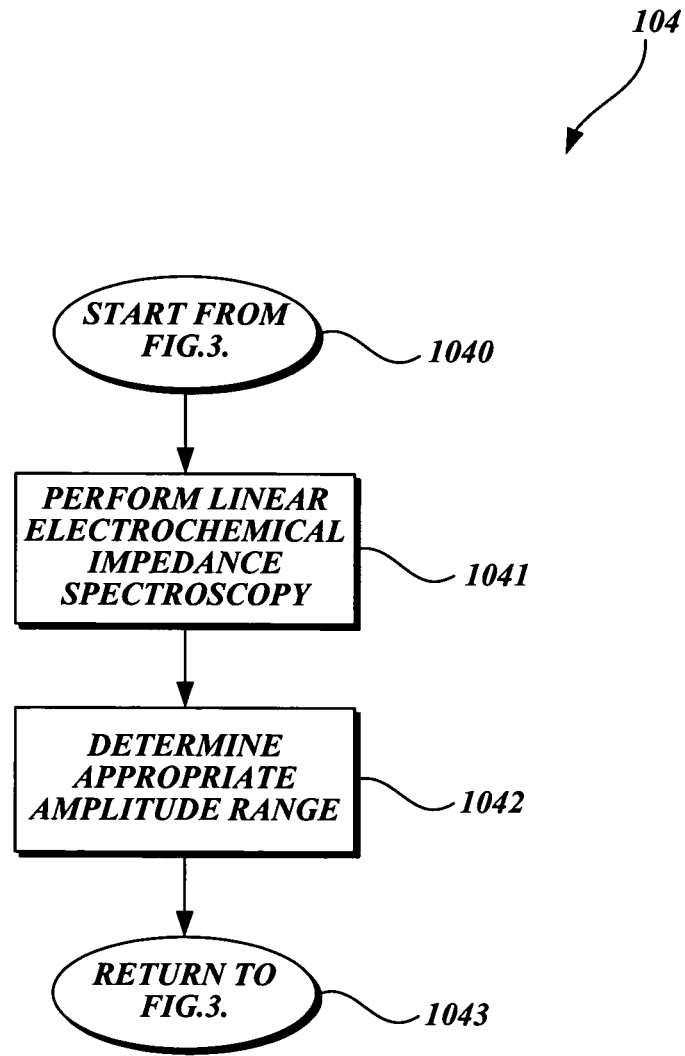
FIG. 7 is a flow diagram of a method for conducting nonlinear electrochemical impedance spectroscopy in accordance with one embodiment of the present invention.

FIG. 7 is a flow diagram of a sub-method 104 for conducting linear electrochemical impedance spectroscopy. The sub-method 104 begins from start block 1040. Start block 1040 is entered from block 104 in FIG. 3. From start block 1040, the sub-method 104 enters block 1041. Block 1041 is for performing linear electrochemical impedance spectroscopy. Linear electrochemical impedance spectroscopy is performed by the application of current perturbation of a small perturbation amplitude. The purpose of linear electrochemical impedance spectroscopy is to obtain an approximation of the range of perturbation amplitudes and frequencies to probe. From block 1041, the sub-method 104 enters block 1042. Block 1042 is for determining the appropriate amplitude range from the current/voltage curve and from linear impedance measurements for each desired perturbation frequency. The appropriate amplitude range is of moderate value when the higher-order harmonics are measurable, and higher-order contributions to each harmonic do not contribute significantly to that harmonic. In one embodiment, the appropriate range can be determined by experiment. For example, an amplitude range can be chosen and analyzed by plotting each harmonic as a function of perturbation amplitude to the power of harmonic in question. If this plot displays linear data, the amplitude regime is moderate; if the plot displays nonlinear data, the amplitude range is too high and should be adjusted. The appropriate amplitude range can be determined by inspection of the system's current/voltage characteristics and linear impedance. In galvanostatic measurements, the maximum perturbation amplitude should be scaled proportionally with the linear impedance as a function of frequency. The maximum amplitude in the determined amplitude range may change as the linear impedance changes over a range of frequencies. From block 1042, the method 104 enters return block 1043. Block 1043 returns to the method 100 of FIG. 3.

Figure 8:
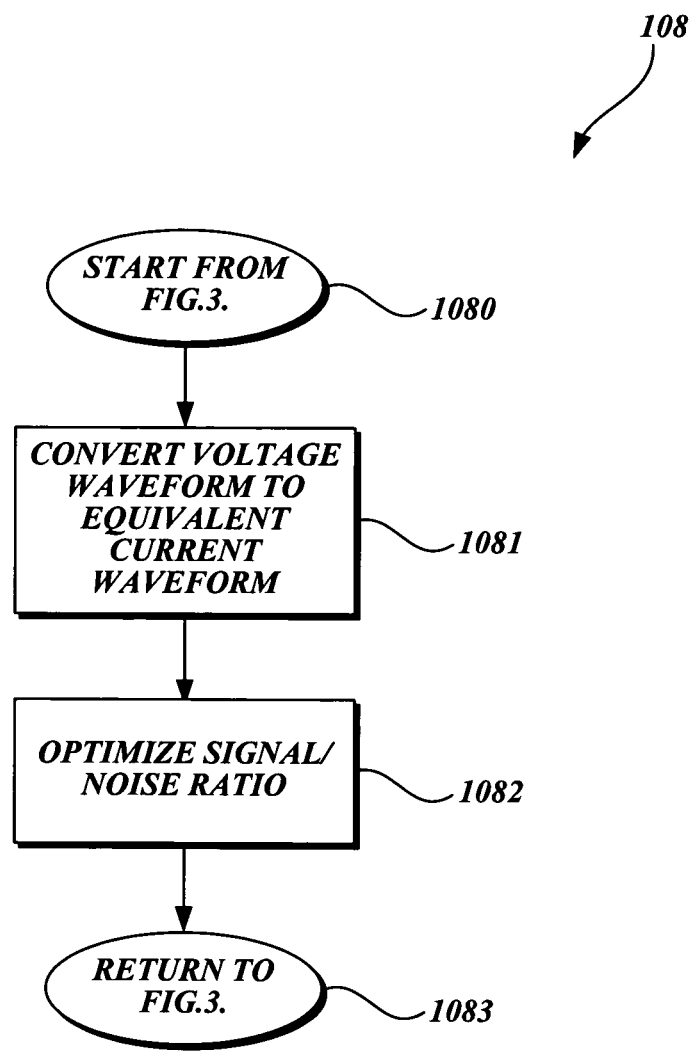
FIG. 8 is a flow diagram of a method for conducting nonlinear electrochemical impedance spectroscopy in accordance with one embodiment of the present invention.

FIG. 8 is a flow diagram of a sub-method 108 for determining the electrochemical interface settings. Electrochemical interface settings are the parameters that are available on the electrochemical interface for manipulating the input and output signals, such as shunt resistor selection, bias handling, signal amplification and attenuation. The sub-method 108 begins from start block 1080. Start block 1080 is entered from block 108 in FIG. 3. From start block 1080, the sub-method 108 enters block 1081. Block 1081 is for converting the voltage waveform to an equivalent current waveform if operating in galvanostatic mode. From block 1081, the sub-method 108 enters block 1082. Block 1082 is for optimizing the signal-to-noise ratio. The signal-to-noise ratio is optimized using signal attenuation and bias rejection. From block 1082, the sub-method 108 enters return block 1083. Block 1083 returns the sub-method 108 to block 108 in FIG. 3.

Figure 9:
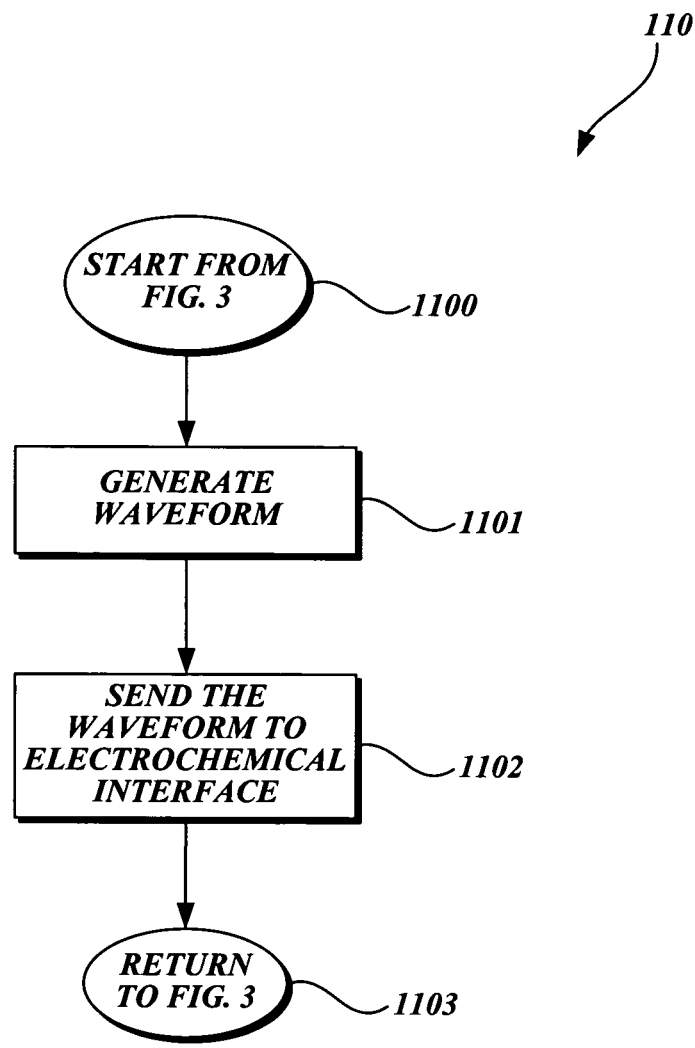
FIG. 9 is a flow diagram of a method for conducting nonlinear electrochemical impedance spectroscopy in accordance with one embodiment of the present invention.

FIG. 9 is a flow diagram of a sub-method 110 for generating waveforms. The sub-method 110 begins at start block 1100. Start block 1100 is entered from block 110 of FIG. 3. From block 1100, sub-method 110 enters block 1101. Block 1101 is for generating a waveform. Generation of a waveform is carried out by using a function generator 16. A suitable function generator 16 is a National Instruments Model No.

5401, for example, but can also be accomplished using a wide range of other standard electronic hardware products. These products usually produce a waveform in terms of voltage, which is converted to a current if the desired perturbation signal is current. A function generator is capable of producing a sinusoidal signal of a predetermined amplitude and predetermined frequency. Function generator 16 receives its instructions from computer 12. From block 1101, the sub-method 110 enters block 1102. Block 1102 is for sending the waveform to the electrochemical interface 20. The electrochemical interface 20 is the potentiostat 20 of FIG. 1. From block 1102, the sub-method 110 enters return block 1103. Block 1103 returns the sub-method 110 to method 100 of FIG. 3.

Figure 10:
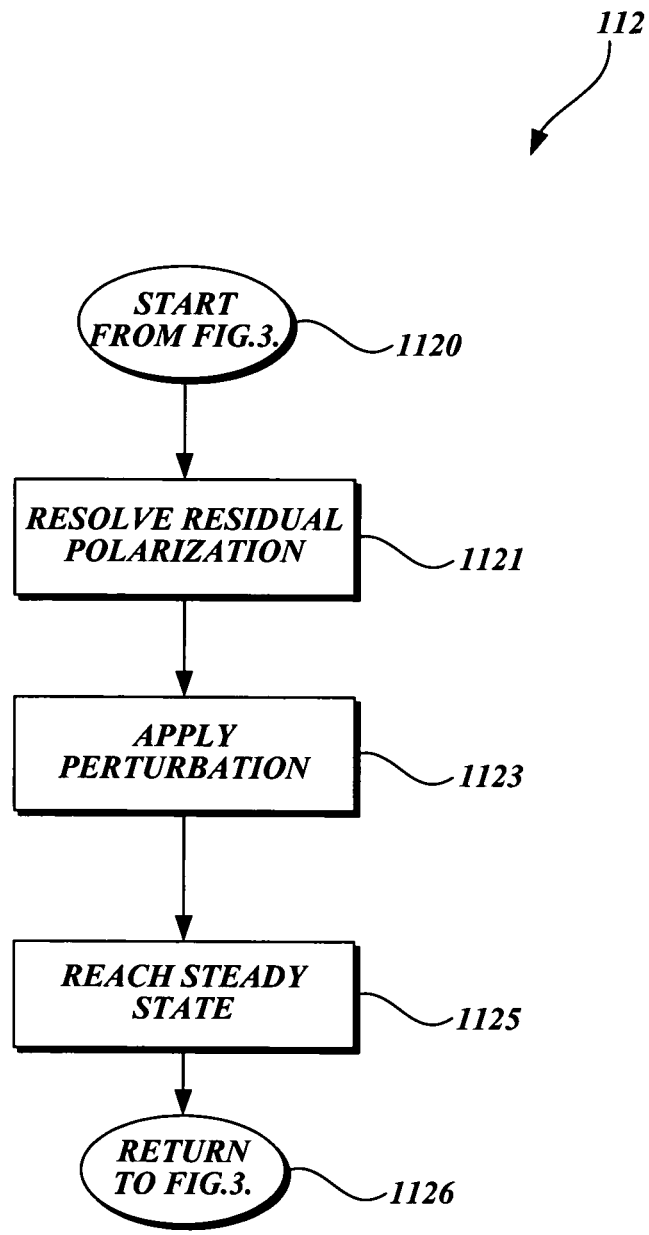
FIG. 10 is a flow diagram of a method for conducting nonlinear electrochemical impedance spectroscopy in accordance with one embodiment of the present invention.

FIG. 10 illustrates a flow diagram of sub-method 112 for applying a perturbation signal. Perturbation signals are of a predetermined sinusoidal perturbation amplitude and frequency. Sub-method 112 begins from start block 1120. Start block 1120 is entered from block 112 of FIG. 3. From start block 1120, the sub-method 112 enters block 1121. Block 1121 is for resolving residual polarization. Residual polarization refers to a polarization in the subject electrochemical system that exists prior to the measurement, and can be due to previous conditions of operation. Residual polarization is resolved in an effort to bring the system to steady-state. From block 1121, the sub-method 112 enters block 1123. Block 1123 is for applying an alternating voltage or current perturbation signal. If the perturbation is desired to be a current signal, the voltage signal from the waveform generation step 1101 is applied across the shunt resistor to convert from an alternating voltage waveform into an alternating current waveform. From block 1123, the sub-method 112 enters block 1125. Block 1125 is for allowing the electrochemical system 32 to reach steady-state. Steady-state is reached by applying the same signal of unvarying amplitude and frequency for a period of time. Steady-state is reached when at least three cycles of the response signal are comparable. When steady-state is reached, the response from the electrochemical system 32 can be measured. From block 1125, the sub-method 112 enters return block 1126. Block 1126 is for returning sub-method 112 to block 112 of FIG. 3.

Figure 11:
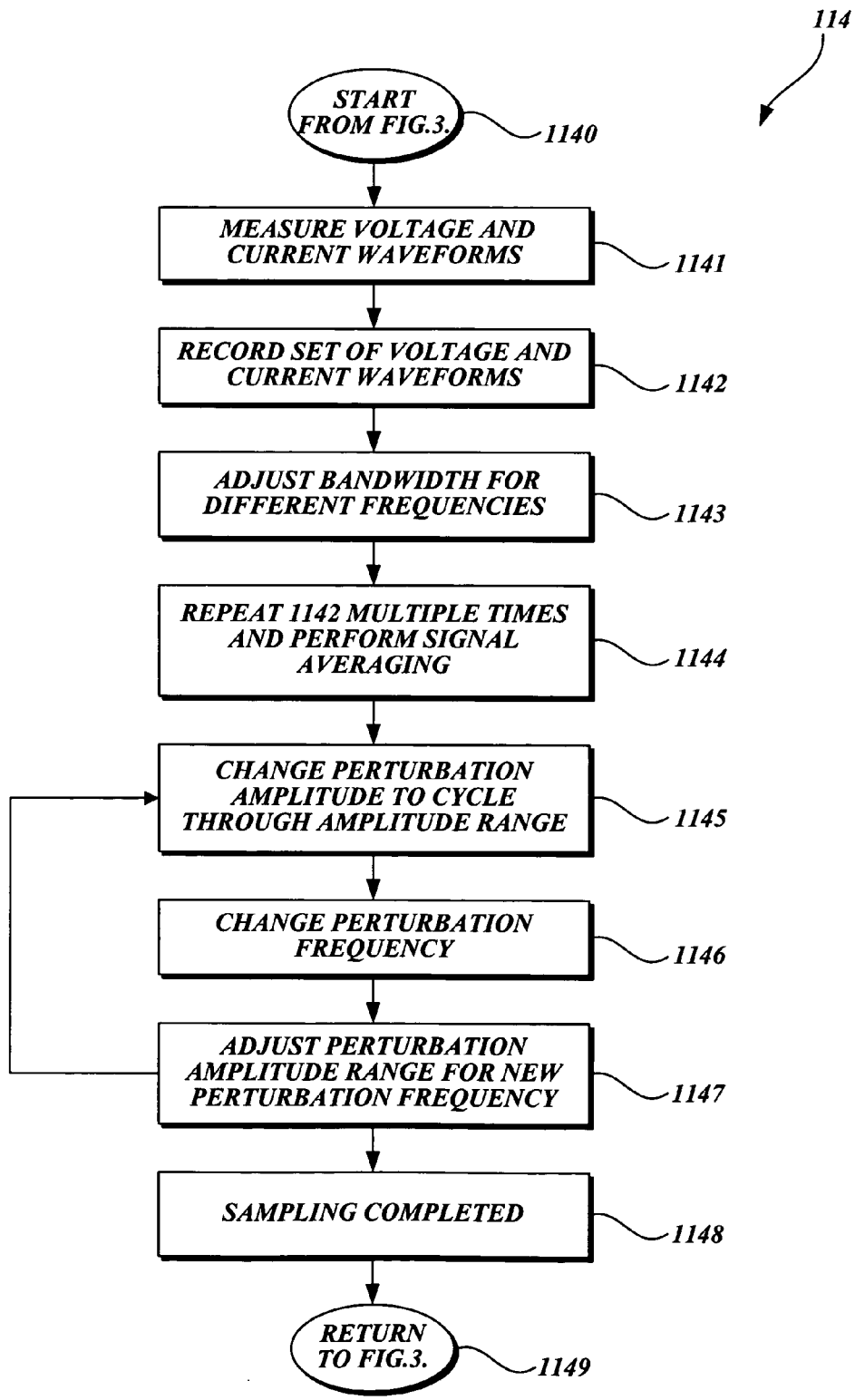
FIG. 11 is a flow diagram of a method for conducting nonlinear electrochemical impedance spectroscopy in accordance with one embodiment of the present invention.

FIG. 11 is a flow diagram of a sub-method 114 for data acquisition. Sub-method 114 begins from start block 1140. Start block 1140 is entered from block 114 of FIG. 3. From start block 1140, the sub-method 114 enters block 1141. Block 1141 is for measuring the voltage and current waveforms in response to the perturbation signal. From block 1141, the method 114 enters block 1142. Block 1142 is for recording a first set of voltage and current waveforms for a first perturbation signal at a first perturbation amplitude and perturbation frequency. From block 1142, the sub-method 114 enters block 1143. Block 1143 is for adjusting the acquisition bandwidth for different frequencies. The bandwidth, which is directly related to the sampling frequency, is adjusted to capture fundamental harmonics and at least one higher-order harmonic. From block 1143, the sub-method 114 enters block 1144. Block 1144 is for taking multiple readings of the response current and voltage at the same perturbation amplitude to perform signal averaging. Signal averaging reduces the noise of the data. From block 1144, the method enters block 1145. Block 1145 is for changing the perturbation amplitude to cycle through the amplitude range. For every perturbation frequency that is probed, the perturbation amplitude is varied from a small value within a range that is, at least, broad enough to include sampling in a range of moderate amplitudes, where the higher-order harmonics are measurable, as discussed in block 1042. The perturbation signal is cycled through a number of amplitudes at each frequency in discrete intervals. The system is allowed to reach steady-state before recording a new set of response voltage and current waveforms after changing the perturbation amplitude of the perturbation signal. From block 1145, the sub-method 114 enters block 1146. Block 1146 is for changing the perturbation frequency. As with the perturbation amplitude, the perturbation frequency is sampled through a perturbation frequency range at discrete intervals. Once every amplitude perturbation is probed at one frequency, a different perturbation frequency can be probed. From block 1146, the sub-method 114 enters block 1147. Block 1147 is for adjusting the perturbation amplitude for each new perturbation frequency as determined by step 1042. Operating at a different perturbation frequency may necessitate that a different amplitude range be sampled at the new frequency. A range of amplitudes should be broad enough to cover the moderate amplitudes. Since moderate amplitude is determined to exist later in the process, the sampling of perturbation amplitudes and perturbation frequencies can be an interactive process. If the perturbation amplitudes do not result in response signals that indicate the perturbation amplitudes were in the moderate range, the process can return to apply a different range of amplitudes for each frequency. Block 1147 returns to block 1145 to cycle through another, possibly different amplitude range at the new frequency. When all the sampling is completed, the sub-method 114 enters block 1148. Block 1148 is for indicating that sampling is completed, data has been collected, and the method 100 is ready to begin the data processing aspect. From block 1148, the sub-method 114 enters return block 1149. From return block 1149, the sub-method 114 returns to block 114 in FIG. 3.

Figure 12:
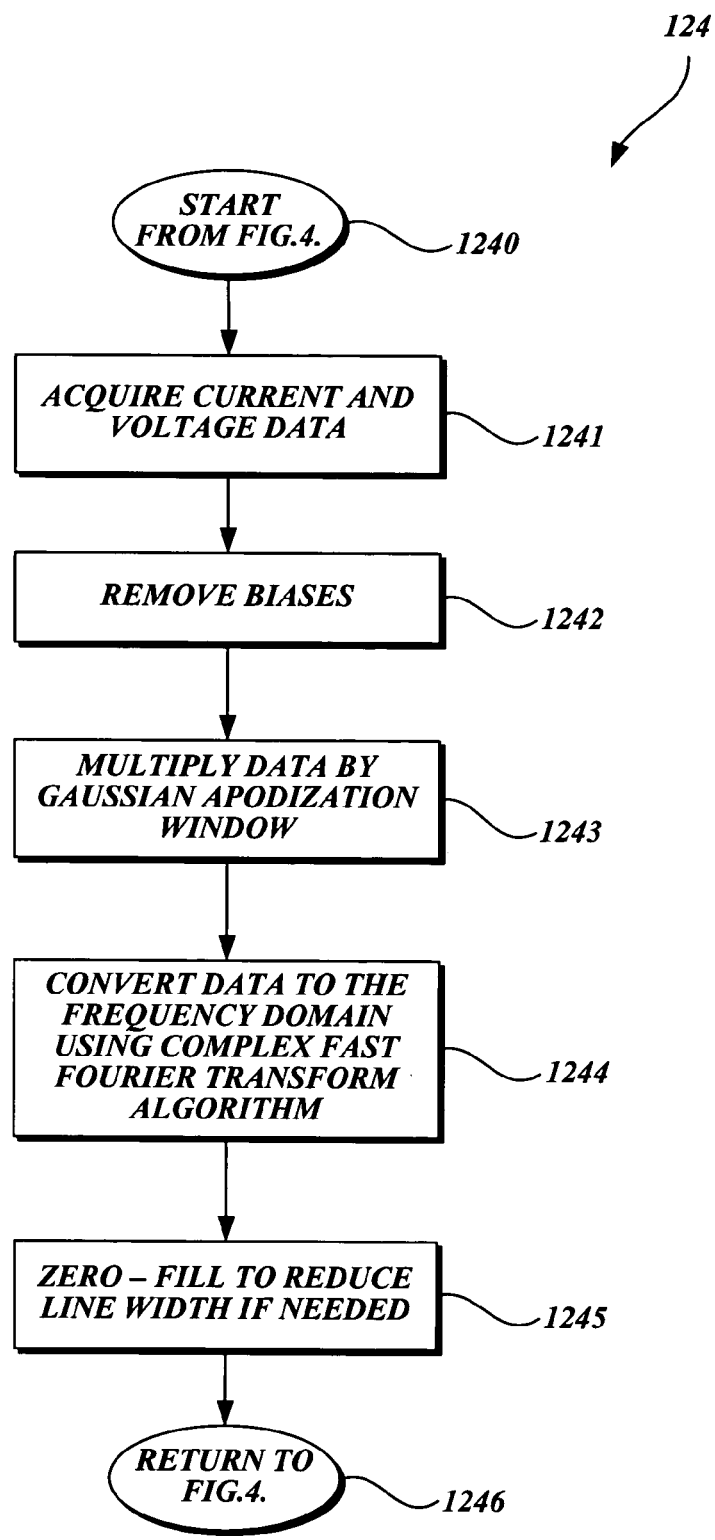
FIG. 12 is a flow diagram of a method for conducting nonlinear electrochemical impedance spectroscopy in accordance with one embodiment of the present invention.

FIG. 12 is a flow diagram of a sub-method 124 for data processing. Sub-method 124 begins at start block 1240. Start block 1240 is entered from block 124 of FIG. 4. From start block 1240, the sub-method 124 enters block 1241. Block 1241 is for acquiring the perturbation signal and response signal data that results from the sampling routine performed in earlier blocks. A preferred environment for processing data is in a digital processor of computer 12. As the response signal is analog, the signal is passed through the analog-to-digital converter 18. Digitized data is processed in computer 12. Such data can be imported into the software modules of computer 12. From block 1241, the sub-method 124 enters block 1242. Block 1242 is for removing biases. This step can be performed via an algorithm residing within the program module of computer 12. A bias is a baseline value of current or voltage that offsets the AC signal waveforms from zero. Removing biases is important because the response signal waveforms are preferably centered around zero to optimize the Gaussian apodization step of the data processing. From block 1242, the sub-method 124 enters block 1243. Block 1243 is for multiplying the perturbation and response data by a Gaussian apodization window so that they can be compared in the same form later in the data processing. Generally, "apodization" refers to a mathematical technique used to reduce the Gibbs phenomenon ("ringing") that is produced in spectral data. While Gaussian apodization is one such mathematical technique, other apodization techniques are within the scope of the present invention. One embodiment of an equation that represents a representative Gaussian apodization window is:

$$W(t) = \exp\left(-\left(\frac{\omega t}{2\pi b}\right)^2\right). \quad (1)$$

Figure 21:
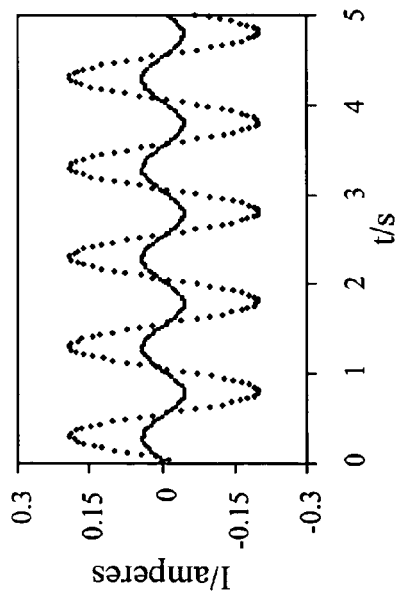
FIG. 21 is a representative plot of the Gaussian-apodized current data at an amplitude of 200 mA.
Figure 22:
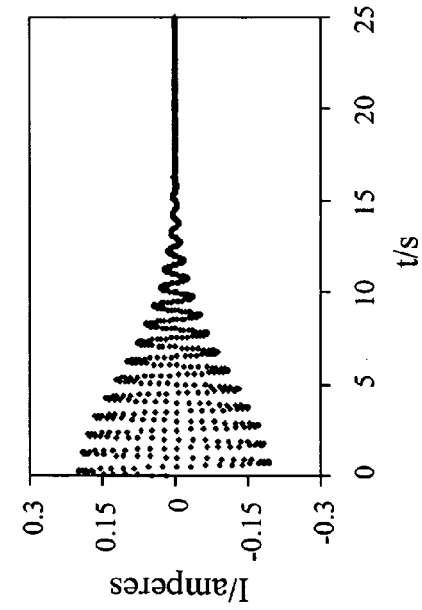
FIG. 22 is a representative plot of the Gaussian-apodized potential response at a current perturbation amplitude of 200 mA.

In this application, the same equation is numbered consistently throughout. The result of Gaussian-apodized data when plotted in the time domain is a waveform that has a decaying signal. A representative plot of apodized data is illustrated in FIGS. 21 and 22. From block 1243, the sub-method 124 enters block 1244. Block 1244 is for converting the Gaussian-apodized data into transformed data in the frequency domain using a complex fast Fourier transform algorithm (FFT). There are other transform tools, such as Laplace Transforms, that could accomplish the same task as a fast Fourier transform algorithm. When representing spectral data, i.e., data resulting from application of a perturbation signal, it is possible to represent the response signal in different domains. In this application, the time domain and frequency domain are used. In the time domain, current and/or voltage signals are represented as the current or voltage signal amplitude versus time. In the frequency domain, current and/or voltage signals are represented as current and/or voltage signal amplitude versus frequency. A transform function is used to convert data from the time domain to the frequency domain, while the inverse transform function is used to convert data from the frequency domain to the time domain. The fast Fourier transform is a discrete Fourier transform algorithm which reduces the number of computations needed for N points from $2N^2$ to 2NlgN, where lg is the base-2 logarithm. One embodiment of a mathematical expression that represents a transform function is:

$$F(\omega) = \int_{-\infty}^{\infty} f(t)e^{-j2\pi\omega t}dt. \quad (1a)$$

The above equation is a simple equation for a Fourier transform. However, the Fast Fourier Transform algorithm is more complicated and is not described by an equation for brevity in this application. From block 1244, the sub-method 124 enters block 1245. Block 1245 is for zero-filling the transformed, apodized current and voltage data to reduce line width. Zero filling increases the data size by adding zeros to the end of the data set; this can be useful in two ways. The first is that if the number of data points collected is not a power of 2, zero filling will expand the size of the data set to the next higher power of 2, a preferred step for performing the Fast Fourier Transform algorithm. Zero filling can also be used to enhance digital resolution by increasing the data size. Block 1245 is optional if the data size is to the power of 2, but can be useful in enhancing resolution. Representative plots of transformed, apodized current and voltage data are illustrated in FIGS. 23-31. The specific amplitude and frequency of each plot is described above in the section titled Description of the Drawings. From block 1245, the sub-method 124 enters return block 1246. Block 1246 returns the sub-method 124 to block 124 in FIG. 4.

Figure 13:
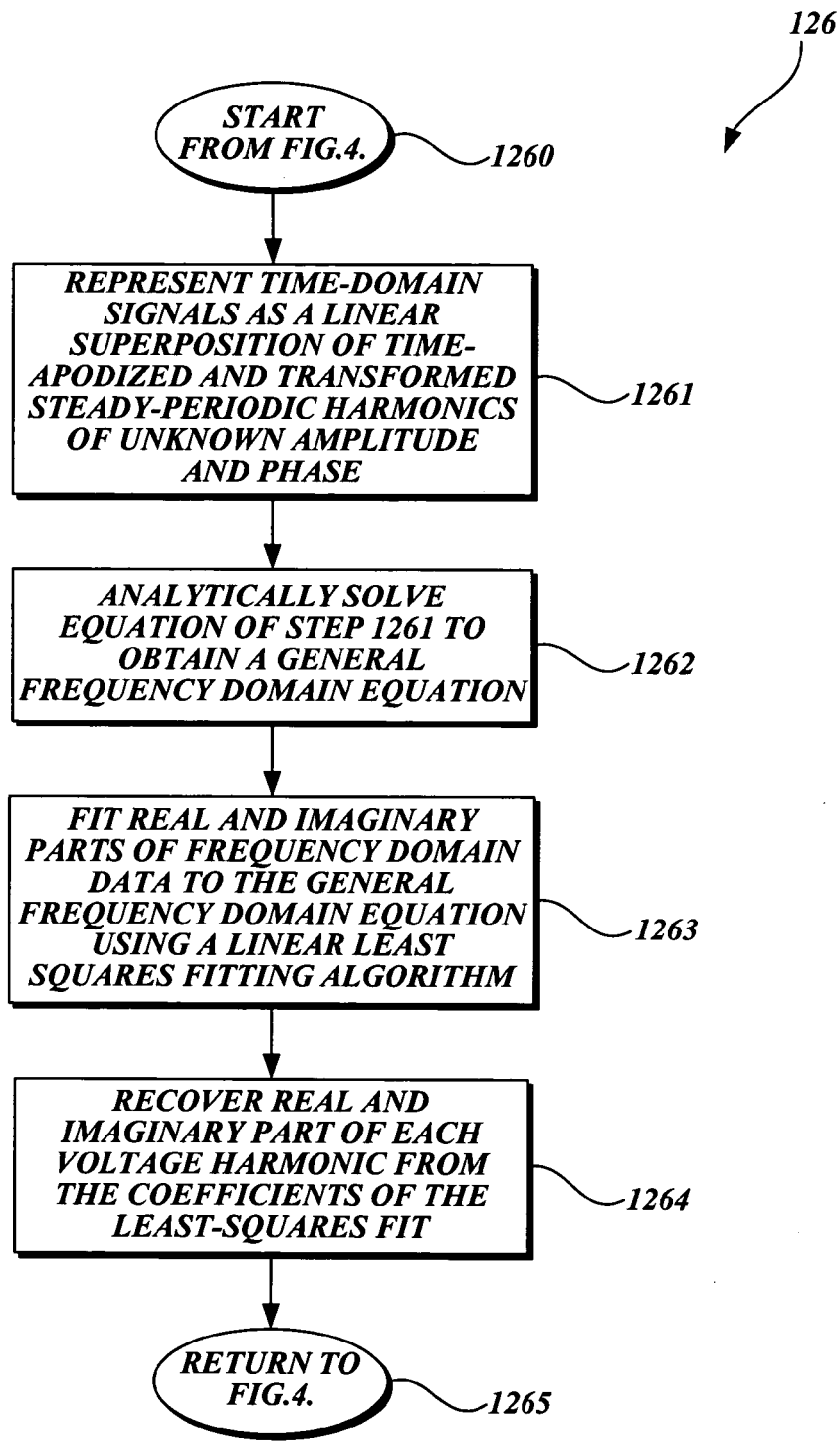
FIG. 13 is a flow diagram of a method for conducting nonlinear electrochemical impedance spectroscopy in accordance with one embodiment of the present invention.

FIG. 13 is a flow diagram of sub-method 126. Sub-method 126 is for simultaneously fitting the transformed, apodized data of block 124 to a general frequency domain equation.

Sub-method 126 begins at start block 1260. Start block 1260 is entered from block 126 of FIG. 4. From start block 1260, the sub-method 126 enters block 1261. Block 1261 is for representing the time-domain perturbation and response signals as a linear superposition of steady-state periodic harmonics of unknown amplitude and phase. Although the harmonics can be readily observed using the apodized and transformed frequency-domain data, lower-order harmonics often create a baseline distortion for the (usually much smaller) higher-order harmonics, making it inconvenient to quantify each harmonic individually. To circumvent this problem, the time domain signals of the perturbation and response were expressed mathematically as a linear superposition of steady-periodic harmonics of unknown amplitude and phase, block 1261. From block 1261, the sub-method 126 enters block 1262. Block 1262 is for analytically solving the equation generated in block 1261 to obtain a general frequency domain equation. A general frequency domain equation is a mathematical expression that defines the harmonic behavior of the electrochemical system 36, in unknown terms representing the first order harmonic contribution and contributions of higher-order harmonics that are resonant with the first order harmonic, and higher-order harmonics greater than one (1), and the contributions of the higher-order harmonics that are resonant for each higher-order harmonic greater than one (1). One representative mathematical expression for expressing the time domain voltage response signal from the electrochemical system 36 is:

$$V(\tilde{i}, \tilde{\omega}, t) = \frac{1}{2}\sum_{k=0}^{\infty} \hat{V}_k(\tilde{i}, \tilde{\omega})\exp(jk\tilde{\omega}t) + \hat{V}_{-k}(\tilde{i}, \tilde{\omega})\exp(-jk\tilde{\omega}t) \quad (2a)$$

where $\tilde{\omega}$ and $\tilde{i}$ are the frequency and amplitude of the frequency perturbation, and $\hat{V}_{\pm k} = \hat{V}'_k \pm j\hat{V}''_k$ are complex Fourier coefficients corresponding to each harmonic (the term j denoting $\sqrt{1}$). A prime denotes the real part of the Fourier coefficient, and a double prime represents the imaginary part.

The equations in this application that use the coefficient denoted "V" represent a galvanostatic system. However, in accordance with the present invention, NLEIS can be operated both potentiostatically and galvanostatically. If NLEIS is operated potentiostatically, the "V" coefficients in the equations can be renamed as "I" coefficients because the response in a potentiostatic operation is the current, or "I." Accordingly, the general frequency equation, which serves as a theoretical expression of the experimental data, is time-apodized and transformed so it can be compared to the experimental data in the same format, for both "V" and "I"; however, only the equation for "V" is represented. It is to be appreciated that a similar equation is generated for "I."

Time-apodization and Fourier-transformation of Equation (2a) yields the general frequency domain equation:

$$\hat{V}(\tilde{i}, \tilde{\omega}, \omega) = \frac{1}{2}\sum_{k=0}^{\infty} \hat{V}'_k(G_k(\omega) + G_{-k}(\omega)) + \hat{V}''_k(D_k(\omega) - D_{-k}(\omega)) + \quad (2b)$$
$$\frac{j}{2}\sum_{k=0}^{\infty} \hat{V}''_k(G_k(\omega) - G_{-k}(\omega)) + \hat{V}'_k(-D_k(\omega) - D_{-k}(\omega))$$

where $$G_k(\omega) = \frac{b\sqrt{\pi}}{\tilde{\omega}}\exp\left(\frac{-(\omega - k\tilde{\omega})^2\pi^2b^2}{\tilde{\omega}^2}\right) \quad (2c)$$

$$D_k(\omega) = \frac{b\sqrt{\pi}}{\tilde{\omega}} \exp\left(\frac{-(\omega - k\tilde{\omega})^2 \pi^2 b^2}{\tilde{\omega}^2}\right) \text{erfi}\left(\frac{(\omega - k\tilde{\omega})\pi b}{\tilde{\omega}}\right) \quad (2d)$$

and erfi(x) is the imaginary error function and is related to the error function by erfi(x)=−j erf(x).

Figure 31:
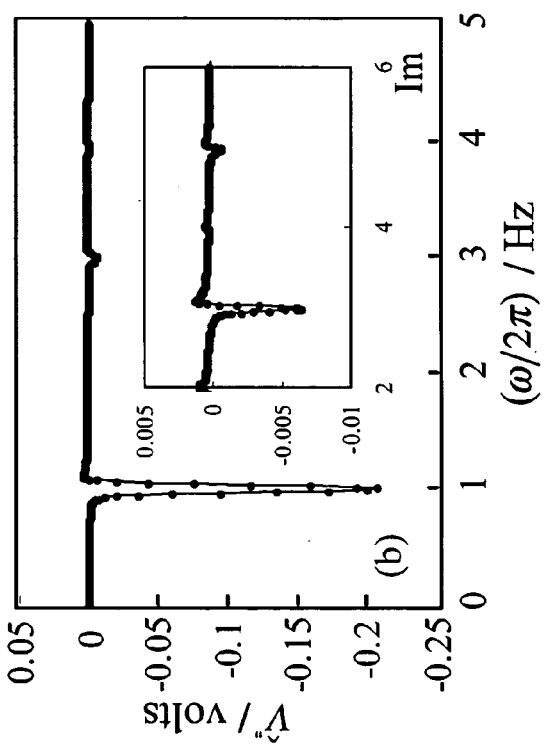
FIG. 31 illustrates representative plots of the Fourier-transformed imaginary potential for a current perturbation of 1.0 Hz and 200 mA, wherein the raw data (symbols) are shown with least squares fit data (line), with inset plots at an expanded scale near the higher-order harmonics.
Figure 30:
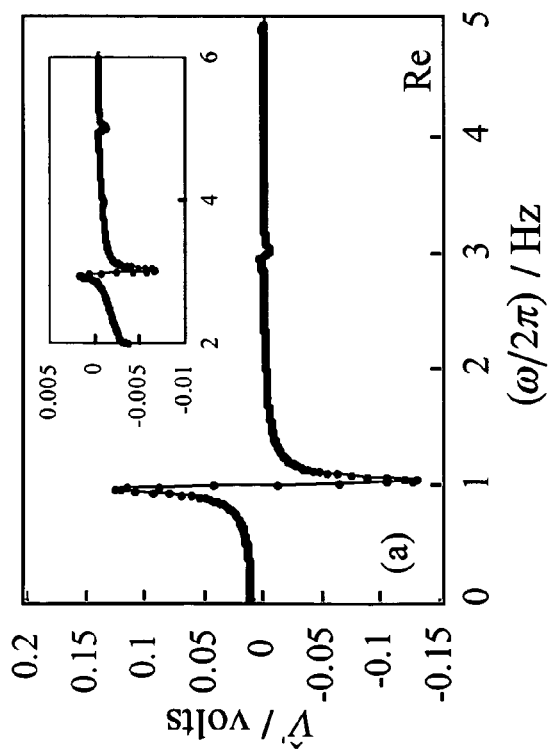
FIG. 30 illustrates representative plots of the Fourier-transformed real potential for a current perturbation of 1.0 Hz and 200 mA, wherein the raw data (symbols) are shown with least squares fit data (line), with inset plots at an expanded scale near the higher-order harmonics.
Figure 34:
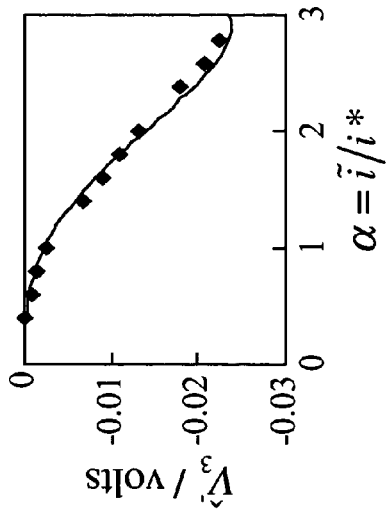
FIG. 34 is a representative plot of the real third potential harmonic as a function of dimensionless current modulation amplitude, for a perturbation frequency of 1.0 Hz with experimental results (symbols) shown with the polynomial fit (line) to Equations 3a and 3b.
Figure 35:
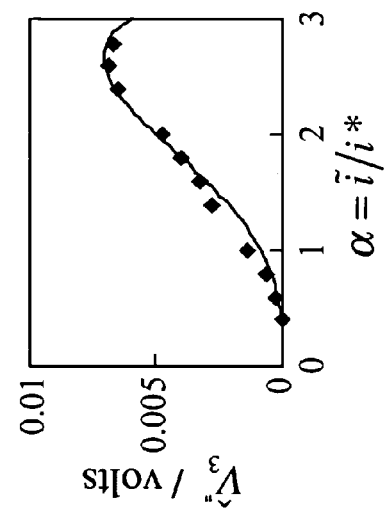
FIG. 35 is a representative plot of the imaginary third potential harmonic as a function of dimensionless current modulation amplitude, for a perturbation frequency of 1.0 Hz with experimental results (symbols) shown with the polynomial fit (line) to Equations 3a and 3b.
Figure 32:
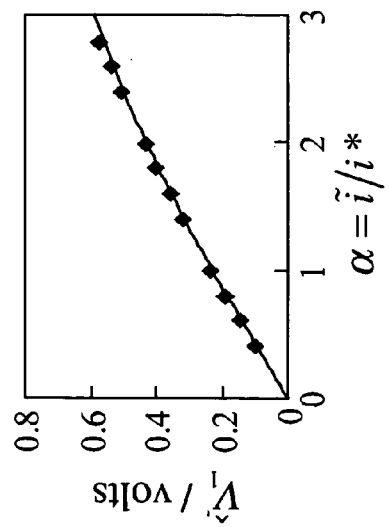
FIG. 32 is a representative plot of the real first (fundamental) potential harmonic as a function of dimensionless current modulation amplitude, for a perturbation frequency of 1.0 Hz with experimental results (symbols) shown with the polynomial fit (line) to Equations 3a and 3b.
Figure 33:
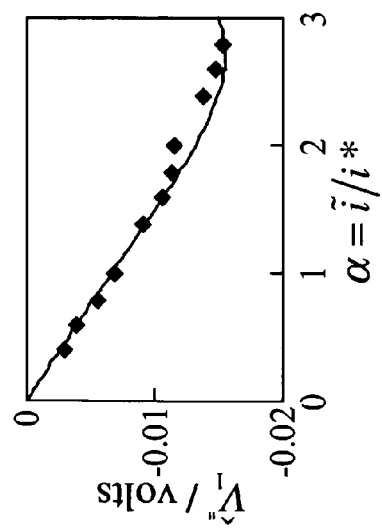
FIG. 33 is a representative plot of the imaginary first potential harmonic as a function of dimensionless current modulation amplitude, for a perturbation frequency of 1.0 Hz with experimental results (symbols) shown with the polynomial fit (line) to Equations 3a and 3b.

From block 1262, the sub-method 126 enters block 1263. Block 1263 is for fitting the real part and the imaginary part of the general frequency domain data obtained in block 1245 to the general frequency domain Equation (2b) using a fitting technique, such as a linear least squares fitting algorithm. A linear least squares algorithm finds the best-fitting curve to describe the frequency-domain current and voltage data by minimizing the sum of the squares of the offsets. A linear least squares algorithm depends on coefficients that can be adjusted to find the best fit. When fitting the current frequency domain data to Equation (2b) in a potentiostatic operation, the adjustable coefficients are $I'_k$ and $I''_k$, where k=1-5, for example. When fitting the voltage frequency domain data to Equation (2b) the adjustable coefficients are $V'_k$ and $V''_k$ where k=1-5. The parameter k is discontinued at 5, because harmonics above the fifth can be difficult to distinguish from the noise. However, in other embodiments, k can be greater than 5. The parameter k is a marker that indicates the Fourier coefficient of the k" order harmonic of either voltage or current. Although a linear least squares fitting algorithm can be used, other algorithms are within the scope of the present invention. By fitting the real and imaginary parts of the frequency-domain data to Equation (2b) using linear least squares, the real and imaginary part of each voltage (or current) harmonic to the desired order in k can be recovered simultaneously. Examples of plots resulting from the least squares fitting procedure to the fifth order are shown in FIGS. 30 and 31.

From block 1263, the sub-method 126 enters block 1264. Block 1264 is for recovering the real and imaginary part of each voltage harmonic from the coefficients in a galvanostatic operation, or from the current harmonic in a potentiostatic operation. The symbols for these coefficients are $V'_k$, $V''_k$, $I'_k$, and $I''_k$ of the least squares fit. The real and imaginary parts of the voltage or current harmonics are recovered by selection from the set of coefficients produced by the fitting algorithm. Step 1264 includes selecting the coefficients and appropriately labeling them real and imaginary for each harmonic. From block 1264, the sub-method 126 enters return block 1265. Return block 1265 returns the sub-method 126 to block 126 in FIG. 4.

Figure 14:
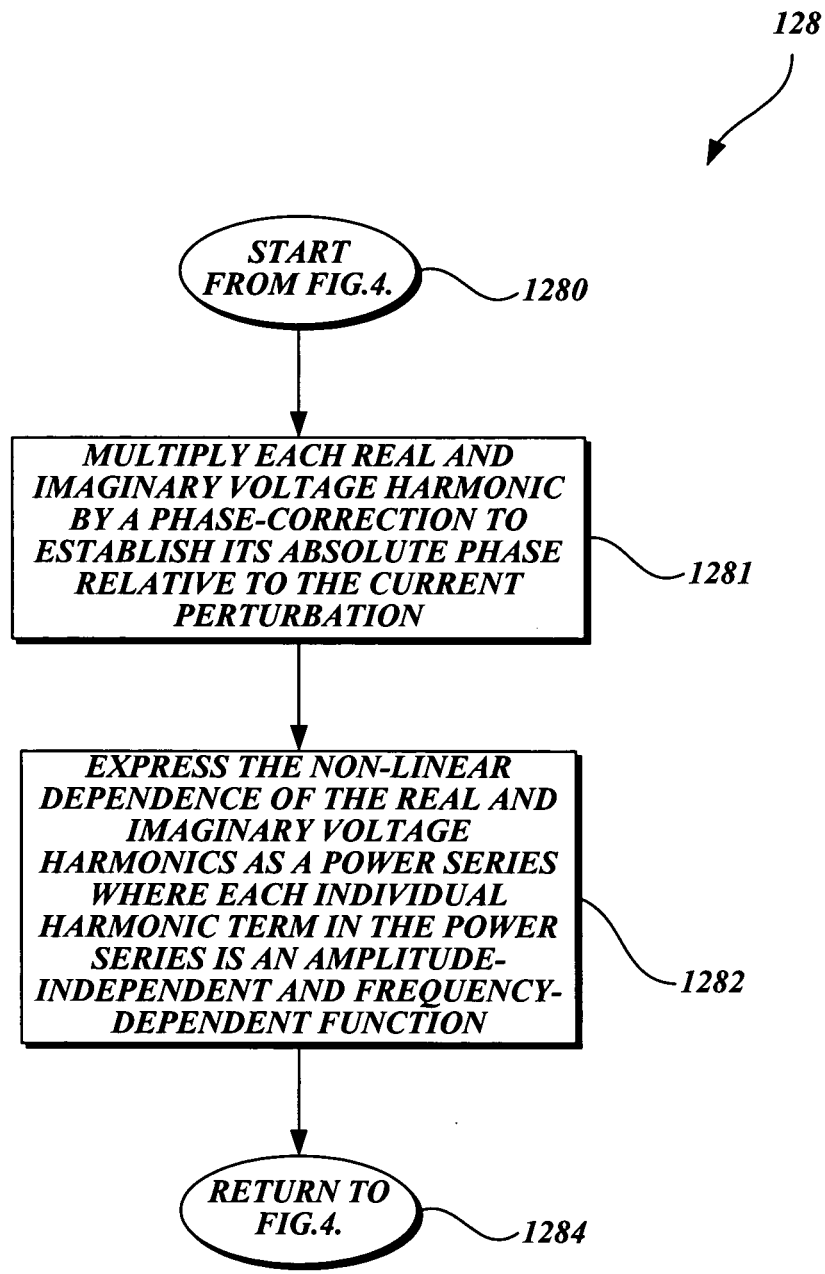
FIG. 14 is a flow diagram of a method for conducting nonlinear electrochemical impedance spectroscopy in accordance with one embodiment of the present invention.

FIG. 14 is a flow diagram of sub-method 128 for phase correcting the harmonic Fourier coefficients of the response from the fit of the data to the general frequency domain equation. Sub-method 128 starts from start block 1280. Start block 1280 is entered from block 128 of FIG. 4. From start block 1280, the sub-method 128 enters block 1281. Block 1281 is for multiplying each real and imaginary response harmonic Fourier coefficient by a phase correction to establish the absolute phase relative to the perturbation. Since the response and perturbation were acquired synchronously, each response harmonic is multiplied by a first order phase correction $\exp(-j\phi_1)$ in order to establish its absolute phase relative to the perturbation. If galvanostatically, $\phi_1$ is obtained from the measured current harmonic coefficients $I'_1$ and $I''_1$. If operated potentiostatically, the parameter $\phi_1$ is obtained from the measured voltage harmonic coefficients $V'_1$ and $V''_1$. The parameter $\phi_1$ is a phase factor representing the point in the perturbation cycle where data acquisition was begun (t=0).

From block 1281, the sub-method 128 enters block 1282. Block 1282 is for expressing the nonlinear dependence of the real and imaginary harmonic coefficients of the response as a power series, where each individual harmonic term in the power series is an amplitude-independent and frequency-dependent function. Because the electrochemical system 36 is nonlinear, the magnitude of each response harmonic $\hat{V}_k(\tilde{i}, \tilde{\omega})$ generally depends nonlinearly on the perturbation amplitude. This nonlinear dependence can be expressed as a power series in amplitude. A representative example of the power series for a galvanostatically operated system is:

$$\hat{V}_k(\tilde{i}, \tilde{\omega}) = \sum_{r=1}^{\infty} \alpha^{k+2r-2} \hat{V}_{k,k+2r-2}(\tilde{\omega}) \quad (2e)$$

where $\alpha = \tilde{i}/i^*$ is the current perturbation amplitude, nondimensionalized based on i*, a real constant having units of current density that characterizes the onset of nonlinearity in the system if operated galvanostatically. However if the experiment is operated potentiostatically $\alpha = \tilde{v}/v^*$, where v* is a real constant having units of volts-area that characterizes the onset of nonlinearity in the system. In other embodiments, alpha can be set equal to the value of the perturbation (i* or v* equal to one) in order to perform a dimensional analysis of the onset of nonlinearity. A characteristic value defines a scale to simplify the physical description of the system 36. The characteristic time of a system is the time it takes for the system to undergo a specific change; for example, the time it takes for the system to respond to the applied perturbation. The characteristic length of a system is a representative length of a physical system; for example, the thickness of an electrode. The characteristic current is, for example, defined as the magnitude of the current at which the system becomes significantly nonlinear. The characteristic voltage is defined, for example, as the magnitude of the response to a current perturbation of the characteristic current. The characteristic resistance is related to the characteristic current and characteristic voltage; resistance equals voltage divided by current. Electrochemical impedance measurements experimentally yield the characteristic resistance, as the width of the arc in the impedance plot (see FIG. 36) and characteristic time, as the inverse of the peak frequency obtained from the same impedance plot (see FIG. 36). By comparison of experimentally derived characteristic values to the definitions in Table 1, values for system parameters, such as diffusion coefficient ($D_v$) and reaction rate coefficient (k), can be determined that were previously unknown.

For example, as with the Fourier coefficients $\hat{V}_k(\tilde{i},\tilde{\omega})$, each term in the power series $\hat{V}_{k,m}(\tilde{\omega})$ has both a real and imaginary component $\hat{V}_{k,m} = \hat{V}'_{k,m} + j\hat{V}''_{k,m}$ embodying magnitude and phase. However, the individual harmonic terms $\hat{V}_{k,m}(\tilde{\omega})$ are amplitude independent and, thus, have the advantage of being purely frequency-dependent functions (like impedance measured at low amplitude). The impedance $Z(\tilde{\omega}) = \hat{V}_{1,1}(\tilde{\omega})/i^*$ is related by definition to the first order contribution to the first harmonic of the voltage through the constant i* for galvanostatic operation. To determine the individual harmonic terms $\hat{V}_{k,m}$, amplitude perturbations can be measured for each frequency probed and then each harmonic term $\hat{V}_k$ fit to the finite power series according to Equation (2e). One term beyond that desired can be included in the polynomial fit in order to absorb error due to higher-order terms. According to the invention, a range of sampling of perturbation amplitudes can be selected so that within such range the perturbation amplitude is proportional to a characteristic value of the electrochemical system, such as characteristic current or voltage. In one embodiment, when the response harmonic coefficients for a particular frequency are plotted versus the amplitude of the perturbation signal raised to the power corresponding to the order of the harmonic term, and the plot is substantially linear, the amplitudes can be fit to Equation 2e. The amplitude-independent harmonics can be extracted from the fit. All amplitude-independent harmonics measured under all frequencies measured compose the measured harmonic structure of the electrochemical system. From block 1282, the sub-method 128 enters return block 1284. Return block 1284 returns sub-method 128 to block 128 of FIG. 4.

Figure 15:
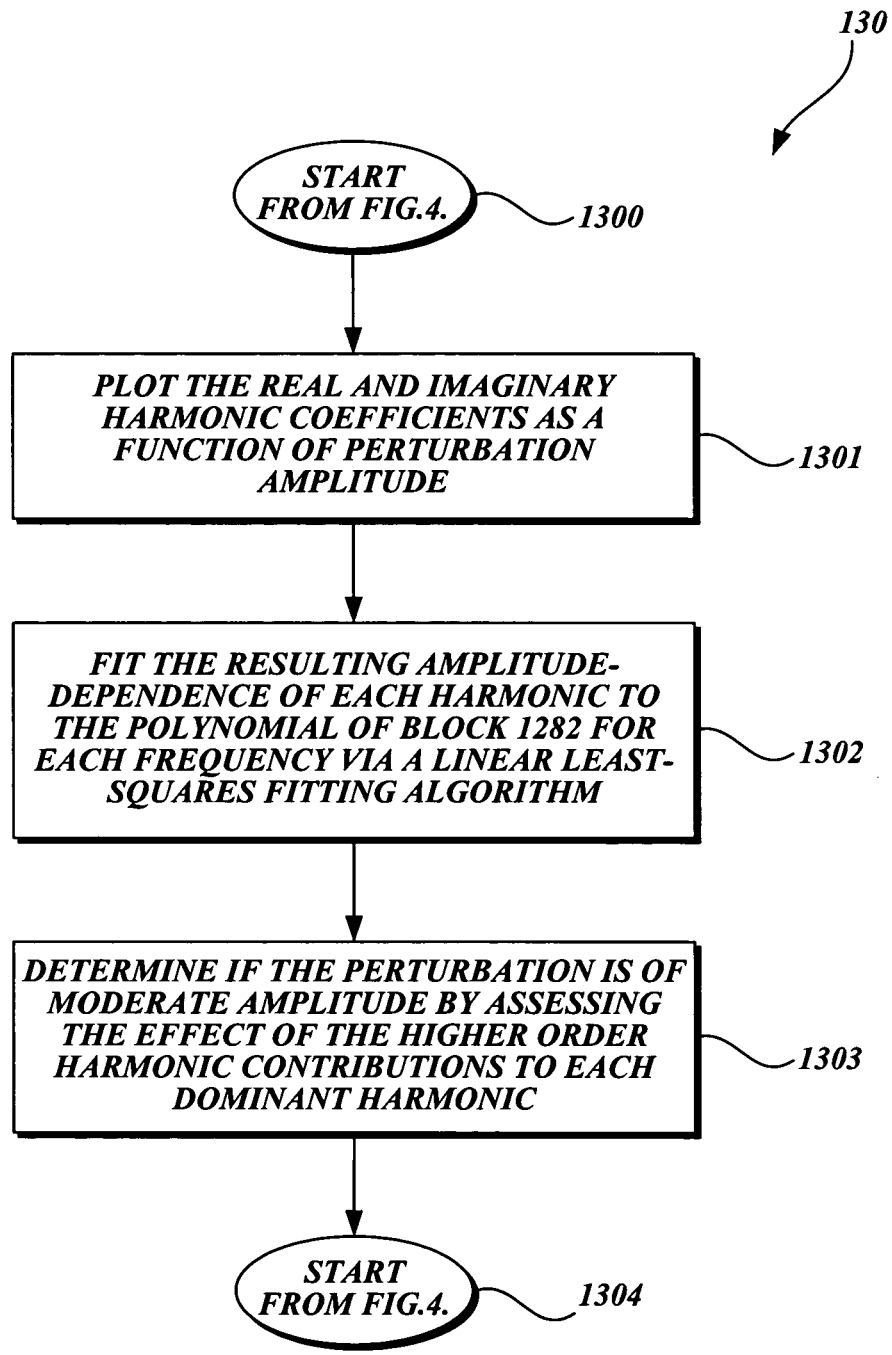
FIG. 15 is a flow diagram of a method for conducting nonlinear electrochemical impedance spectroscopy in accordance with one embodiment of the present invention.

FIG. 15 is a flow diagram of sub-method 130 for the extraction of amplitude independent harmonic coefficients, such as $\hat{V}_{k,m}(\tilde{\omega})$ of Equation (2e). Sub-method 130 begins at start block 1300. Start block 1300 is entered from block 130 of FIG. 4. From start block 1300, the sub-method 130 enters block 1301. Block 1301 is for plotting the real and imaginary harmonic coefficients $\hat{V}_k(\tilde{i},\omega)$ as a function of the perturbation amplitude. Representative plots of the real and imaginary harmonic coefficients are illustrated in FIGS. 32-35 as the symbols, or points. A plurality of plots can be derived from each real and imaginary harmonic term of the first order and from higher orders by plotting these against the perturbation. In step 1301, the harmonic coefficients are being plotted versus the perturbation in order to fit the amplitude dependence in step 1302. The harmonic coefficients are plotted versus the perturbation values raised to the power of the harmonic in step 1303.

From block 1301, the sub-method 130 enters block 1302. Block 1302 is for fitting the resulting amplitude dependence of each real and imaginary harmonic coefficient to the polynomial of block 1282 (Equation (2e)) via a linear least-squares fitting algorithm for each frequency. Representative plots of the curve fit are seen in FIGS. 32-35 as the line. The goal of this is to extract the amplitude-independent harmonic coefficients, $\hat{V}_{k,m}(\tilde{\omega})$, from this fit.

From block 1302, the sub-method 130 enters block 1303. Block 1303 is for determining if the perturbation is of moderate amplitude by assessing the effect of the higher-order harmonic contributions to each dominant harmonic. One means for determining moderate amplitude is to plot the real $\hat{V}'_k$ and imaginary $\hat{V}''_k$ parts of the first order harmonic and of every higher-order harmonic versus the perturbation current amplitude raised to the power corresponding to the order of the harmonic term. Where the plot is proportional to a characteristic value or substantially linear indicates the moderate amplitude regime. A substantially linear plot is representative of moderate amplitude and is the preferred range of perturbation signal sampling. The data beyond the substantially linear portion of the plot indicates effects from harmonics of higher order to the particular subject harmonic (if the real component of the third-order harmonic was plotted against i* raised to the third power, then the nonlinear portion of the data would indicate contributions from the seventh, ninth, etc., higher-order harmonics) and can be convoluted by these effects. In one embodiment, the range of perturbation amplitudes for which the plot of the amplitude-dependent response harmonic terms versus perturbation amplitude is substantially linear defines moderate amplitude perturbation signals and is the preferred range for sampling. That part of the response signal data that behaves linearly with respect to the characteristic value is deemed to occur at moderate amplitudes of the perturbation signal. The data collected that are within the moderate amplitude range can reliably be used to create an amplitude-independent harmonic structure (FIGS. 37-42). Otherwise, if the data collected fall outside of the moderate range, the data can be affected by significant contributions from higher-order harmonics and, thus, cannot be extracted from Equation (2e) into an amplitude-independent harmonic in step 130. Determining the moderate amplitude regime also provides a check to determine whether the initial sampling of perturbation amplitudes encompassed the moderate amplitude regime. If not, additional sampling can be done to include sampling in the moderate amplitude range. From block 1303, the sub-method 130 enters return block 1304. Return block 1304 returns sub-method 130 to block 130 of FIG. 4.

Figure 16:
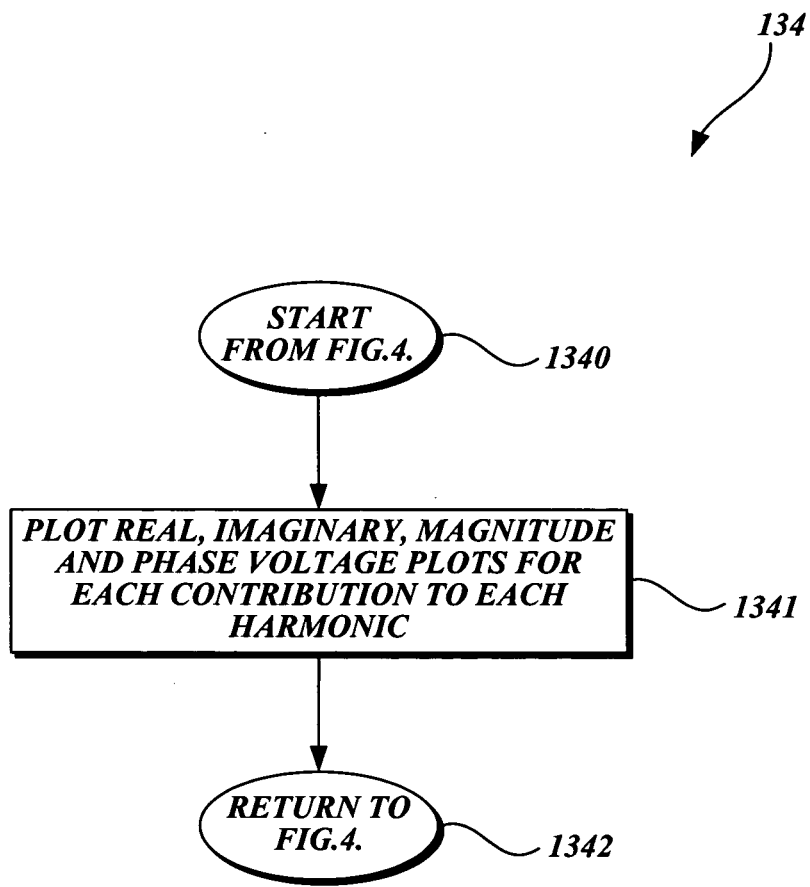
FIG. 16 is a flow diagram of a method for conducting nonlinear electrochemical impedance spectroscopy in accordance with one embodiment of the present invention.

FIG. 16 is a flow diagram for a sub-method 134 for plotting the results. Sub-method 134 starts from start block 1340. Start block 1340 is entered from block 134 of FIG. 4. From start block 1340, the sub-method 134 enters block 1341. Block 1341 is for plotting the real, imaginary, magnitude and phase of current or voltage, depending on the measurement method (i.e., whether a galvanostatic or potentiostatic operation) for each contribution to each amplitude-independent harmonic. Representative plots are illustrated in FIGS. 37-42. FIGS. 32-35 show the amplitude dependence of the harmonics for a single frequency and show the corresponding polynomial fit. This procedure may be repeated over the entire range of frequencies, resulting in the amplitude-independent harmonic structures illustrated in FIGS. 37-42. As used in this application, a harmonic structure may take many representations. A test for moderate amplitude involves the linearity of the plots in step 1303. If the plots meet the test for moderate amplitude, the $\hat{V}_{k,m}(\tilde{\omega})$ terms are plotted against frequency to create a Bode plot (in one example representation), or the real and imaginary components are plotted against each other to create a Nyquist plot, etc. These are just two ways of representing the amplitude-independent harmonic structure. Electrochemical impedance spectroscopy yields the response of the first harmonic to a sinusoidal perturbation. When the first harmonic response is plotted as a function of perturbation frequency in the form of either a Bode plot (FIGS. 37-42, solid triangle symbols) or as a Nyquist plot (FIG. 36, solid square symbols), the experimentally obtained structure of the first harmonic is displayed. The data is the same, though it is plotted a different way, and both plotting methods illustrate the structure of the first harmonic as obtained from experiment. The line in FIG. 36 indicates the structure of the first harmonic derived from theory. In FIGS. 37-42, the lines that fit to the triangle symbols also represent the structure of the first harmonic derived from theory. In contrast, nonlinear electrochemical impedance spectroscopy yields the response of the first contribution to the first harmonic ($U_{1,1}$ in FIGS. 36-42), along with higher-order harmonics ($U_{1,3}$ and $U_{3,3}$ in FIGS. 37-42) to a sinusoidal perturbation. The general term "harmonic structure" is either the measured harmonic structure or harmonic structure derived from theory. The harmonic structure measured by experiments includes the structure of all harmonics obtained from NLEIS experiments; this is displayed in, but not limited to, FIGS. 37-42 as the set of solid triangle symbols, solid square symbols, and solid circle symbols. The harmonic structure derived from theory is shown as lines in FIGS. 37-42, and is derived from a mathematical model. The harmonic structure derived from theory could be infinite, but we limit it to those harmonics that were measurable by experiment.

FIGS. 37-42 also include plots according to various theoretical models that define a known behavior pattern for known processes. The experimental response of the electrochemical system 36 can, therefore, be compared to the models. In one embodiment, the use of NLEIS, according to one embodiment of the invention, is to prove or verify a theoretically derived model of a system. In another embodiment, the use of NLEIS according to one embodiment of the invention, the rate-limiting processes of the system 36 can be determined. Plots can be displayed on a display 64 of computer 12 for visual comparison, for example. From block 1341, the sub-method 134 enters the return block 1342. The return block 1342 returns the sub-method 134 to block 134 of FIG. 4.

Figure 17:
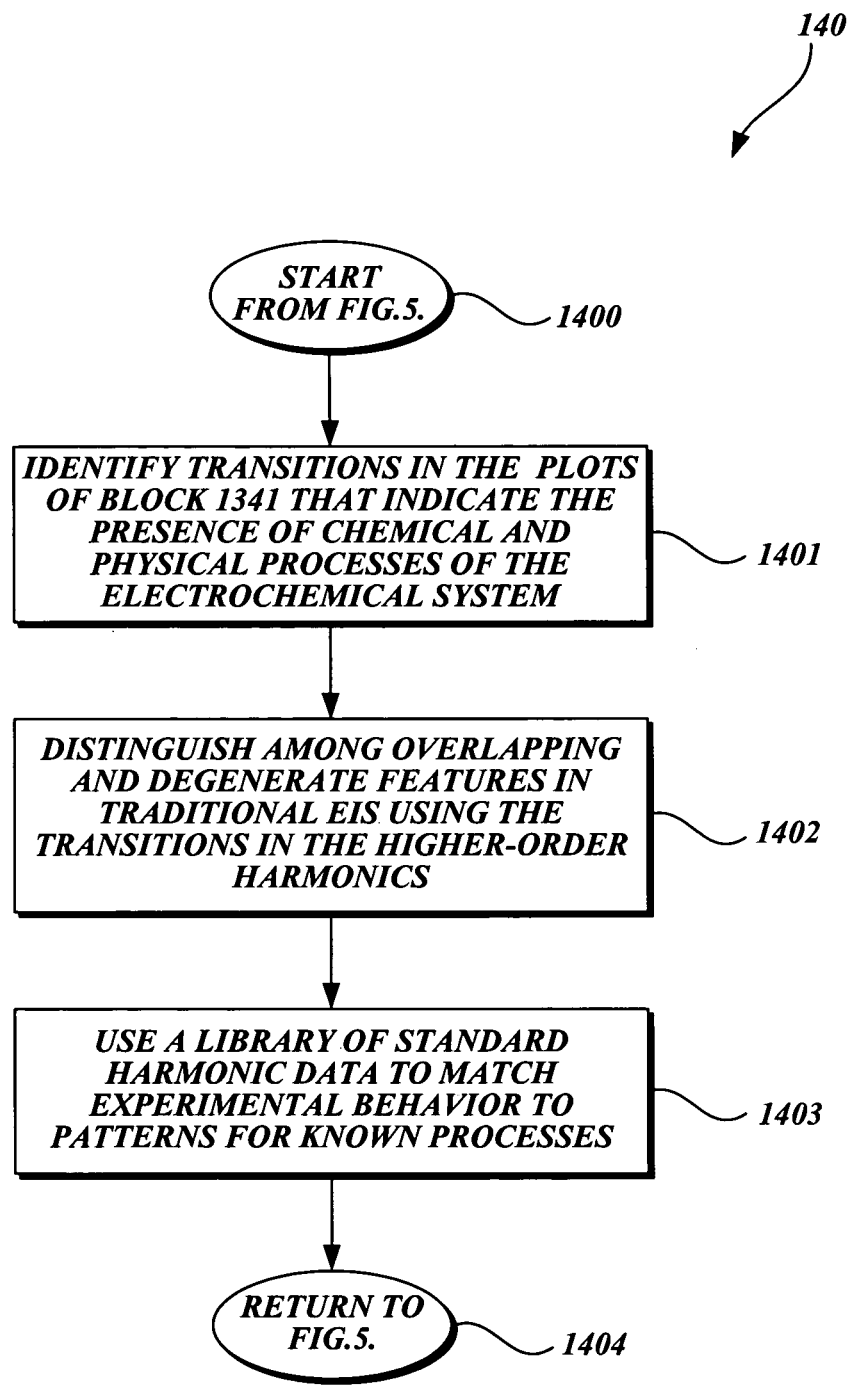
FIG. 17 is a flow diagram of a method for conducting nonlinear electrochemical impedance spectroscopy in accordance with one embodiment of the present invention.

FIG. 17 is a flow diagram of a sub-method 140 for performing analysis. One embodiment of analysis includes a method for determining rate-limiting electrochemical processes of the electrochemical system 36. The method may include a step for comparing the amplitude-independent harmonic structures to one or more patterns known to describe a rate-limiting electrochemical behavior of the electrochemical system 36. The method includes determining the pattern that best fits the harmonic structure to determine the rate-limiting electrochemical process of the electrochemical system 36. The patterns that describe the electrochemical system 36 behavior may be derived experimentally or analytically. The patterns may pertain to kinetic processes and diffusion processes. Another form of analysis in this step could come from a person with expertise in NLEIS data interpretation. An expert could identify patterns in the experimental data and attribute them to electrochemical behavior (limiting processes) by inspection, separate from a rigorous pattern-matching technique. Sub-method 140 starts at start block 1400. Start block 1400 is entered from block 140 of FIG. 5. From start block 1400, the sub-method 140 enters block 1401. Block 1401 is for identifying transitions in the plots that indicate the presence of chemical and physical processes of the electrochemical system 36. From block 1401, the sub-method 140 enters block 1402. Block 1402 is for distinguishing among overlapping and degenerate features in traditional EIS, using the transitions in the higher-order harmonics. From block 1402, the sub-method 140 enters block 1403. Block 1403 is for using a library of standard harmonic data to match experimental behavior to patterns for known processes. The models can be stored in libraries on the computer's 12 memory and compared against the amplitude-independent harmonic structures plotted in FIGS. 37-42. Several models can be tried to determine which of the models provides the best fit for the harmonic structures derived from performing NLEIS in accordance with one embodiment of the invention. For example, the differences can be determined between the model and the harmonic structure at various points on the plots. An example of an algorithm for finding the model that best fits the experimental data calculates the sum of the squares of the differences. From block 1403, the sub-method 140 enters return block 1404. Block 1404 returns sub-method 140 to block 140 of FIG. 5.

REPRESENTATIVE EXAMPLE

Electrochemical Impedance Spectroscopy (EIS) is used extensively to probe the electrochemical characteristics of solid oxide fuel cell (SOFC) electrodes. While EIS has proven to be a powerful technique for isolating and characterizing electrode response, detailed analysis of EIS data provides only limited insight regarding the specific rate-determining steps governing electrode reaction mechanisms. A major factor limiting the usefulness of EIS data is overlap or dispersion in the frequency domain among physical processes governing electrode reactions, making them difficult to resolve entirely by timescale. Another factor is that different mechanistic models for a given reaction often predict very similar impedance response after the governing equations have been linearized.

This example presents the experimental and theoretical frequency response of porous $La_{0.8}Sr_{0.2}CoO_{3-\delta}$ (LSC-82) on samaria-doped ceria (SDC) at 750° C. in air. LSC-82 on SDC was chosen for this study because this system has already been well studied and modeled using linear EIS. In addition, independent measurements of the thermodynamic, kinetic, and transport properties of LSC-82 have been made over a wide range of conditions. The present analysis concentrates on measurement and modeling of the first and third harmonic contributions to the voltage response. As shown below, these nonlinear harmonics appear to yield additional insight into the possible reaction mechanism not obtainable from the impedance alone.

Oxygen molecules in a SOFC are generally thought to adsorb somewhere onto one or more solid surface(s) where they undergo catalytic and/or electrocatalytic reduction steps to form partially reduced ionic/atomic species. These species must transport along surfaces, or inside the bulk of the electrode to the electrolyte, where they are fully and formally incorporated as electrolytic $O^{2-}$-ions. If, how, and where any of these processes happen, and what step(s) are rate determining for a particular electrode, is only partially understood. One embodiment of the present invention can perform nonlinear electrochemical impedance spectroscopy to investigate the rate-limiting processes.

In order to gain further insight into the mechanisms governing SOFC cathodes, both linear and nonlinear responses were probed. Nonlinear responses were probed via nonlinear electrochemical impedance spectroscopy (NLEIS). NLEIS involves the measurement of nonlinear second and higher-order voltage harmonics resulting from moderate amplitude current perturbations. By the excitation of nonlinear responses and interactions, NLEIS potentially offers improved identification of physical steps via nonlinearity and extent of coupling, as well as timescale.

Experimental

Materials and Characterization

Symmetrical cells including of two porous $La_{0.8}Sr_{0.2}CoO_{3-\delta}$(LSC-82) cathode layers were fabricated by screen-printing and firing LSC-82 ink onto pre-fired dense tape-cast 250 micron thick Sm-doped ceria (SDC) electrolyte. The green SDC tape (79% $CeO_2$, 20% $Sm_2O_3$, 1% $TiO_2$ as a sintering aid), made by Cerametec, Inc. (Salt Lake City), was cut into approximately 2.5 cm×2.5 cm square cells, and fired to greater than 98% density at 1650° C. for 4 hours in air. The LSC-82 ink was prepared from $La_{1-x}Sr_xCoO_{3-\delta}$ powder of composition x=0.2, obtained from Praxair Surface Technologies (Seattle). The ink was made using a three-roll mill, blending the LSC-82 powder with alpha-terpineol, ethyl cellulose, ethanol, and oleic acid (all UHP grade from Alpha-Aesar). LSC electrodes of 1.0 $cm^2$ area were then screen printed onto both sides of the dense electrolyte, and fired in air at 1150° C. for 2 hours. Porous silver current collectors were screen printed onto the LSC electrodes and fired at 900° C. for two hours.

After sintering of the electrodes, the cell was examined with x-ray diffraction (Philips 1820XRD), and found to be single-phase with no X-ray-detectable impurities. A scanning electron microscopy SEM (FEI Sirion) was used to characterize the microstructure of the electrodes and verify the absence of minor second phases. The electrode thickness was determined from SEM analysis to be ~6 microns. Porosity and surface area of the electrodes were estimated based on the thickness, amount printed, and particle size in the SEM micrographs.

Test Set-Up and Nleis Apparatus

Figure 18:
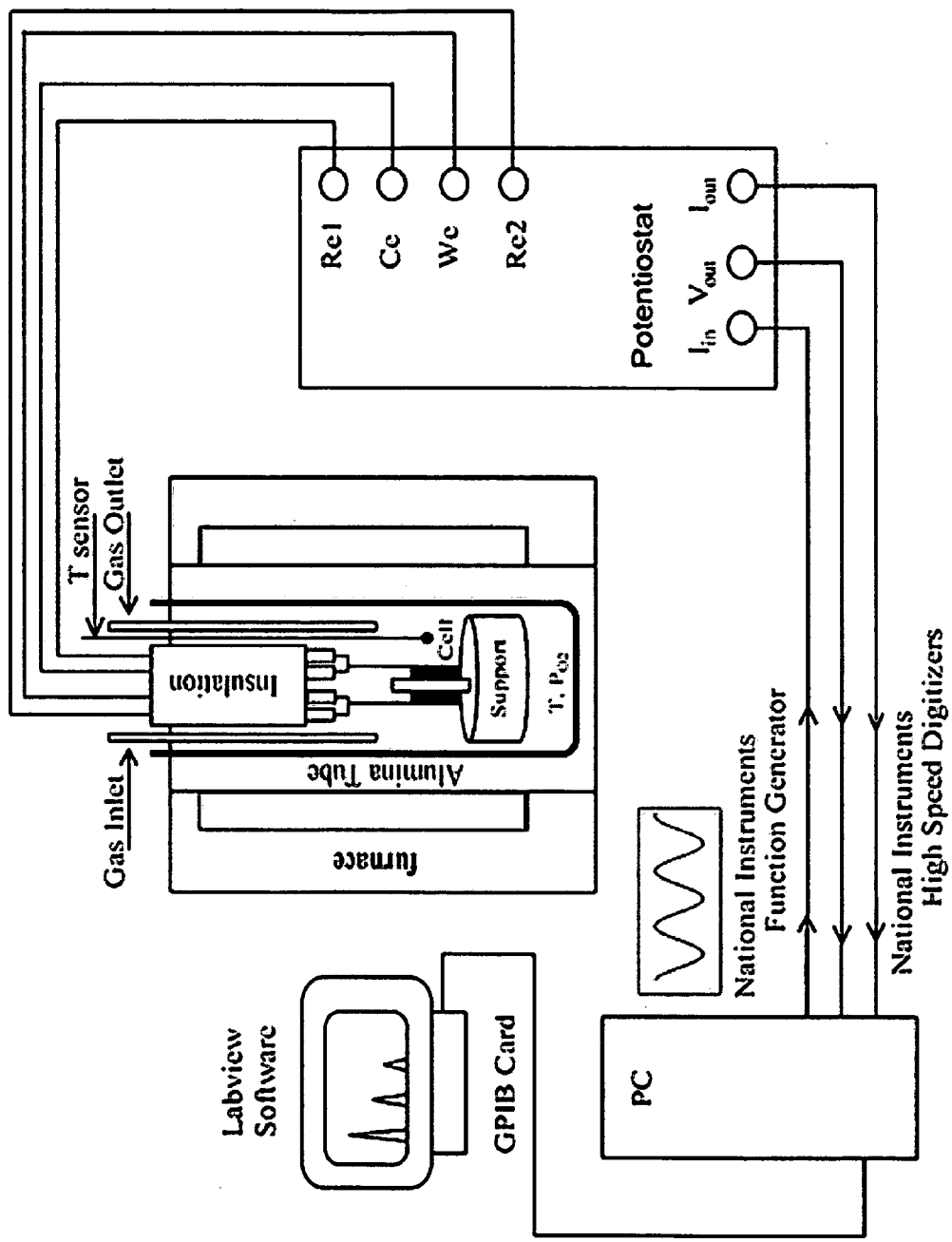
FIG. 18 is a schematic illustration of the apparatus used to conduct NLEIS measurements in accordance with one embodiment of the present invention.

Prior to NLEIS measurements, the linear impedance of the cell was measured galvanodynamically using a Solartron 1287 potentiostat and Solartron 1252A frequency response analyzer (FRA) at 750° C. in air. For NLEIS measurements, the FRA was replaced with a Dell PC containing a National Instruments 5401 function generator linked synchronously to two National Instruments 5911 high-speed digitizers. A schematic of this apparatus is illustrated in FIG. 18. The symmetric cell is supported vertically inside an alumina protection tube, with silver wire leads connected to the current collectors on each side of the cell. Reference leads are connected to the two current leads close to the cell, avoiding wire polarization effects. Temperature is controlled via an external furnace, while $P_{O2}$ is controlled using air or blended gases of $O_2$ in $N_2$ or He. A computer running software known under the designation LABVIEW is used to control the potentiostat, as well as a sinusoidal function generator and two synchronized high-speed digitizers. The signal generator was connected to the POL I/P (set-point) coaxial input of the potentiostat, while the VOUT and IOUT coaxial outputs of the potentiostat were connected to the digitizers. By varying the frequency and amplitude of the generated signal, the resulting voltage response and the current modulation itself could be measured and recorded synchronously. The current was modulated at frequencies between 0.1 Hz and 10,000 Hz, at a zero dc bias. For each frequency, 10 perturbations of varying amplitude were applied. Measurements reported below were made at 750° C. in air.

Signal Acquisition and Analysis

For each amplitude and frequency measurement, the system was modulated for at least three cycles prior to data acquisition to ensure steady periodic behavior. A total of 4096 data points were then collected at an acquisition rate of 40.96 $\tilde{\omega}/2\pi$, where $\hat{\omega}$ is the radial frequency of the current perturbation, providing 100 cycles of current and voltage modulation. FIGS. 19 and 20 show examples of the time-domain data.

In order to define the line width of the subsequent frequency-domain data, the time-domain data were multiplied by a Gaussian apodization window W(t):

$$W(t) = \exp\left(-\left(\frac{\tilde{\omega}t}{2\pi b}\right)^2\right). \tag{1}$$

As shown in FIGS. 21 and 22, apodization transforms the steady periodic time-domain data (of undefined duration) into a time-decaying signal. The application of this transformation results in a frequency-domain signal having a well-defined Gaussian line width proportional to b cycles, and a defined quantity of points, that is controlled by the acquisition rate. For the experiments reported below, an apodization window of b=7.5 cycles was used.

Figure 23:
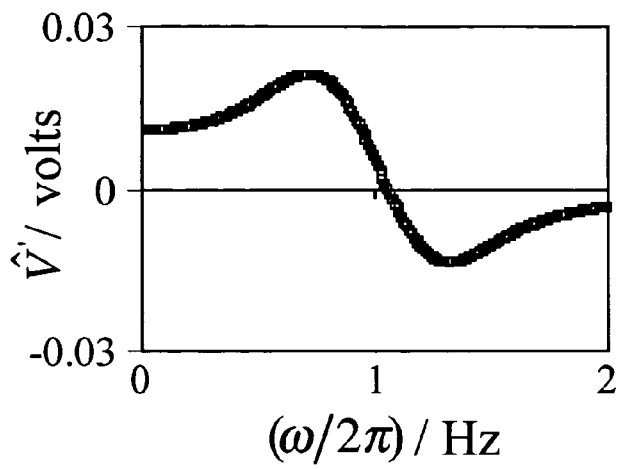
FIG. 23 is a representative plot of the real part of a Fourier-transformed potential corresponding to a current perturbation of 200 mA at 1.0 Hz with a Gaussian apodization window being applied prior to Fourier transformation wherein the window value "b" is equal to 2 cycles.
Figure 24:
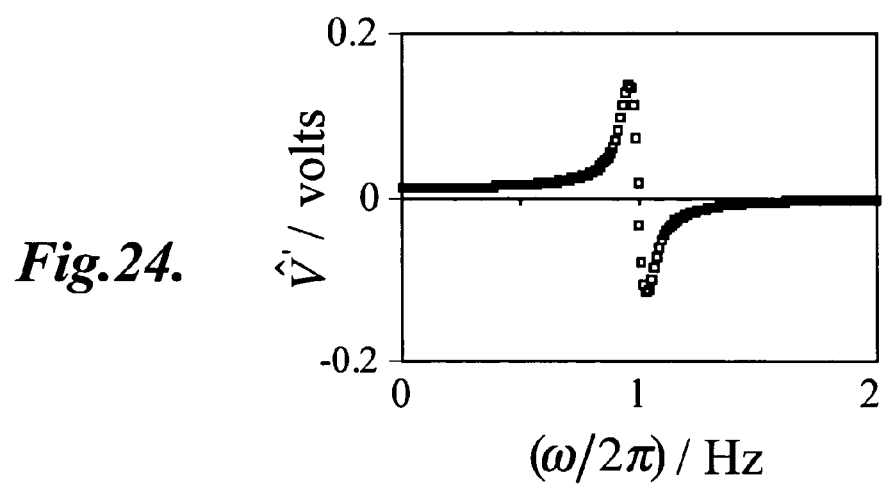
FIG. 24 is a representative plot of the real part of a Fourier-transformed potential corresponding to a current perturbation of 200 mA at 1.0 Hz with a Gaussian apodization window being applied prior to Fourier transformation wherein the window value "b" is equal to 7.5 cycles.
Figure 25:
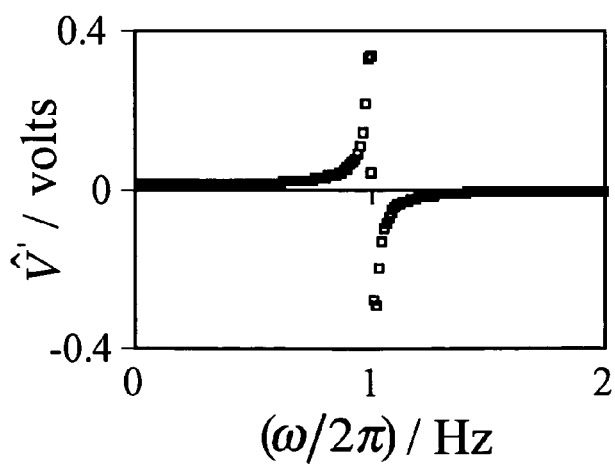
FIG. 25 is a representative plot of the real part of a Fourier-transformed potential corresponding to a current perturbation of 200 mA at 1.0 Hz with a Gaussian apodization window being applied prior to Fourier transformation wherein the window value "b" is equal to 20 cycles.
Figure 28:
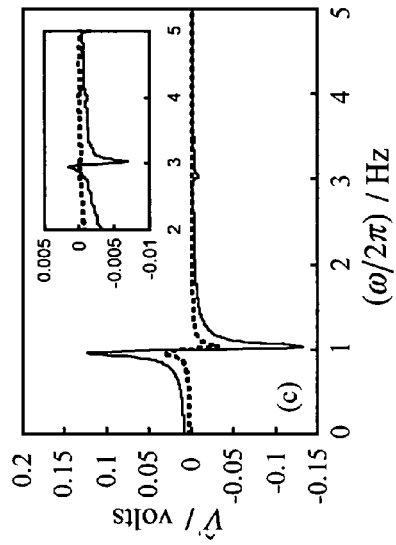
FIG. 28 illustrates representative plots of the Fourier-transformed real potential data at a perturbation frequency of 1.0 Hz and amplitudes of 30 mA ( - - - ) and 200 mA (---), with inset plots at an expanded scale near the higher-order harmonics.
Figure 29:
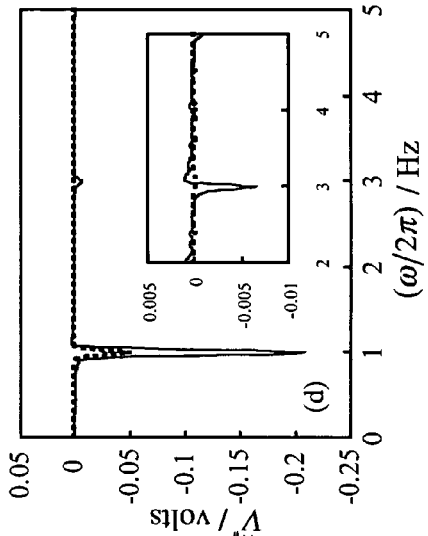
FIG. 29 illustrates representative plots of the Fourier-transformed imaginary potential data at a perturbation frequency of 1.0 Hz and amplitudes of 30 mA ( - - - ) and 200 mA (---), with inset plots at an expanded scale near the higher-order harmonics.
Figure 26:
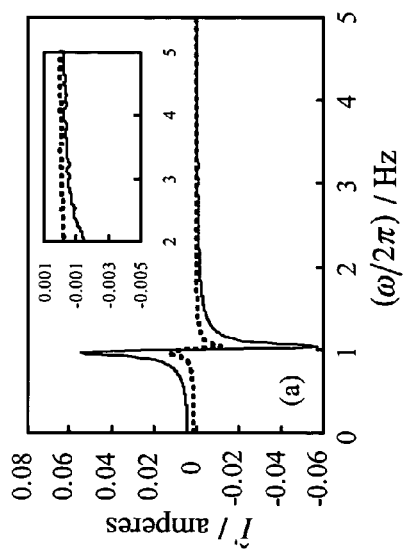
FIG. 26 illustrates representative plots of the Fourier-transformed real current data at a perturbation frequency of 1.0 Hz and amplitudes of 30 mA ( - - - ) and 200 mA (---), with inset plots at an expanded scale near the higher-order harmonics.
Figure 27:
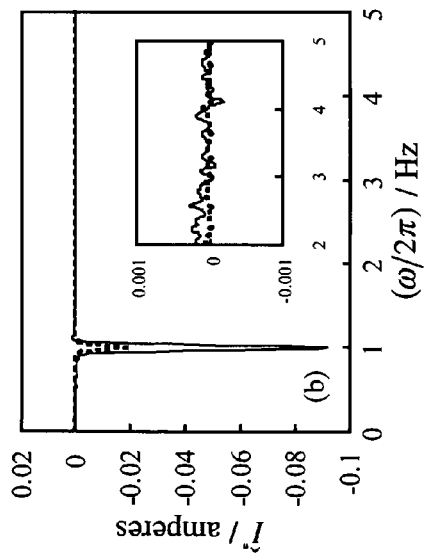
FIG. 27 illustrates representative plots of the Fourier-transformed imaginary current data at a perturbation frequency of 1.0 Hz and amplitudes of 30 mA ( - - - ) and 200 mA (---), with inset plots at an expanded scale near the higher-order harmonics.

To better understand the role of time-apodization, FIGS. 23, 24, and 25 show the real Fourier-transform of the potential response at 1.0 Hz for different values of b. When a mild apodization of b=20 cycles is applied (FIG. 25), the amplitude of the frequency domain signal is maximized, but the exact phase of the signal can be difficult to quantify due to the very few number of points outlining the signal. In contrast, when a rapid decay of b=2 cycles is imposed (FIG. 23), the peak from the first harmonic clearly overlaps the frequency band of the second harmonic, and is also substantially reduced in amplitude. A value of b between 5 and 10 cycles (FIG. 24) provides a compromise of frequency isolation, signal intensity, and number of points defining the Fourier-transformed signal.

Following apodization, the time-domain data were converted to the frequency domain using the complex fast Fourier-transform (FFT) algorithm. FIGS. 26-29 show real and imaginary parts of the Fourier-transformed current and potential, for a modulation frequency of 1.0 cycle/sec, and modulation amplitudes of 30 mA and 200 mA. The Fourier-transformed current has a harmonic signal only at the input frequency, reflecting the fact that the input is a purely sinusoidal waveform. In contrast, the Fourier-transformed potential has a signal at the input frequency as well as integer multiples of the input frequency, indicating that the potential response is nonlinear. The peak at the excitation frequency represents the first order (linear) harmonic of the potential. The peak at k times the excitation frequency corresponds to the $k^{th}$ harmonic. Comparing signals at 30 and 200 mA/cm$^2$, these results show that as the amplitude of the input signal increases, the higher-order harmonics become more clearly discernable, growing nonlinearly out of the background noise.

For a symmetric cell with identical electrodes, harmonic signals of the potential response were found to occur at odd-numbered harmonics (first, third, fifth, etc.). This observation can be attributed to the physical inversion-symmetry of the symmetric cell. In a symmetric system, the response is purely anti-symmetric, corresponding to superposition of odd harmonics generated by the two electrodes, and nullification of even harmonics (second, fourth, sixth, etc.).

Although the harmonics can be readily observed in the frequency-domain data, lower-order harmonics often create a baseline distortion for the (usually much smaller) higher-order harmonics, making it inconvenient to quantify each harmonic individually. To circumvent this problem, the time domain signal were expressed as a linear superposition of steady-periodic harmonics of unknown amplitude and phase:

$$V(\tilde{i}, \tilde{\omega}, t) = \frac{1}{2}\sum_{k=0}^{\infty} \hat{V}_k(\tilde{i}, \tilde{\omega})\exp(jk\tilde{\omega}t) + \hat{V}_{-k}(\tilde{i}, \tilde{\omega})\exp(-jk\tilde{\omega}t) \tag{2a}$$

where $\tilde{\omega}$ and $\tilde{i}$ are the frequency and amplitude of the frequency perturbation, and $\hat{V}_{\pm k}=\hat{V}'_k \pm j\hat{V}''_k$ are complex Fourier coefficients corresponding to each harmonic (the term j denoting $-\sqrt{-1}$). A prime denotes the real part of the Fourier coefficient, and a double prime represents the imaginary part.

Time-apodization and Fourier-transformation of Equation (2a) yields:

$$\hat{V}(\tilde{i}, \tilde{\omega}, \omega) = \frac{1}{2}\sum_{k=0}^{\infty} \hat{V}'_k(G_k(\omega) + G_{-k}(\omega)) + \hat{V}''_k(D_k(\omega) - D_{-k}(\omega)) + \tag{2b}$$

$$\frac{j}{2}\sum_{k=0}^{\infty} \hat{V}''_k(G_k(\omega) - G_{-k}(\omega)) + \hat{V}'_k(-D_k(\omega) - D_{-k}(\omega))$$

where $$G_k(\omega) = \frac{b\sqrt{\pi}}{\tilde{\omega}}\exp\left(\frac{-(\omega - k\tilde{\omega})^2\pi^2 b^2}{\tilde{\omega}^2}\right) \tag{2c}$$

$$D_k(\omega) = \frac{b\sqrt{\pi}}{\tilde{\omega}} \exp\left(\frac{-(\omega - k\tilde{\omega})^2 \pi^2 b^2}{\tilde{\omega}^2}\right) erfi\left(\frac{(\omega - k\tilde{\omega})\pi b}{\tilde{\omega}}\right) \quad (2d)$$

and erfi(x) is the imaginary error function and is related to the error function by erfi(x)=−j erf(x). By fitting the real and imaginary parts of the frequency-domain data to Equation (2b) using linear least squares, the real and imaginary part of each voltage harmonic (to the desired order in k) could be recovered simultaneously. An example of this procedure, to fifth order, is shown in FIGS. 30 and 31.

A similar procedure was used to fit the Fourier-transformed current data, allowing extraction of $\hat{I}_1 = \hat{i} \exp(j\phi_1)$, where $(\phi_1)$, is an arbitrary phase factor representing the point in the perturbation cycle where data acquisition was begun (t=0). Since the voltage and current data were acquired synchronously, each voltage harmonic was multiplied by a first-order phase correction exp ($-jk\phi_1$) in order to establish its absolute phase relative to the current perturbation.

Because the system is nonlinear, the magnitude of each voltage harmonic $\hat{V}_k(\hat{i}, \tilde{\omega})$ generally depends nonlinearly on the current perturbation amplitude. This nonlinear dependence can be expressed as a power series in amplitude:

$$\hat{V}_k(\tilde{i}, \tilde{\omega}) = \sum_{r=1}^{\infty} \alpha^{k+2r-2} \hat{V}_{k,k+2r-2}(\tilde{\omega}) \quad (2e)$$

where $\alpha = \tilde{i}/i^*$ is the current perturbation amplitude, nondimensionalized based on i*, a real constant having units of current density that characterizes the onset of nonlinearity in the system.

As with the Fourier coefficients $\hat{V}_k(\tilde{i}, \tilde{\omega})$, each term in the power series $\hat{V}_{k,m}(\tilde{\omega})$ has both a real and imaginary components $\hat{V}_{k,m} \hat{V}'_{k,m} + j\hat{V}''_{k,m}$ embodying magnitude and phase. However, the individual harmonic terms $\hat{V}_{k,m}(\tilde{\omega})$ are amplitude independent and, thus, have the advantage of being purely frequency-dependent functions (like impedance measured at low amplitude). The impedance, $Z(\tilde{\omega}) = \hat{V}_{1,1}(\tilde{\omega})/i^*$ is related by definition to the first order contribution to the first harmonic of the voltage through the constant i*.

To determine the individual harmonic terms, $\hat{V}_{k,m}$, 10 amplitude perturbations were measured for each frequency, and then each harmonic $\hat{V}_k$ was fit to a finite power series according to Equation (2e). One term beyond that desired is needed in the polynomial fit in order to absorb error due to higher-order terms. For this system, the data was found to be sufficiently well resolved to discern $\hat{V}_{1,1}$, $\hat{V}_{1,3}$, and $\hat{V}_{3,3}$:

$$\hat{V}_1(\tilde{i}, \tilde{\omega}) = \alpha \hat{V}_{1,1}(\tilde{\omega}) + \alpha^3 \hat{V}_{1,3}(\tilde{\omega}) + O[\alpha^5] \quad (3a)$$

$$\hat{V}_3(\tilde{i}, \tilde{\omega}) = \alpha^3 \hat{V}_{3,3}(\tilde{\omega}) + O[\alpha^5]. \quad (3b)$$

FIGS. 32-35 show the amplitude dependence of the harmonics for a single frequency and show the corresponding polynomial fit. This procedure was repeated over the entire range of frequencies, resulting in the amplitude-independent spectra shown in FIGS. 37-42 (where the data have been nondimensionalized as described in the Results/Discussion section below). At frequencies above 400 Hz, the higher-order harmonics became too small to resolve accurately using this procedure, and thus are not reported in the frequency response spectra.

Representative Model Calculations

Figure 36:
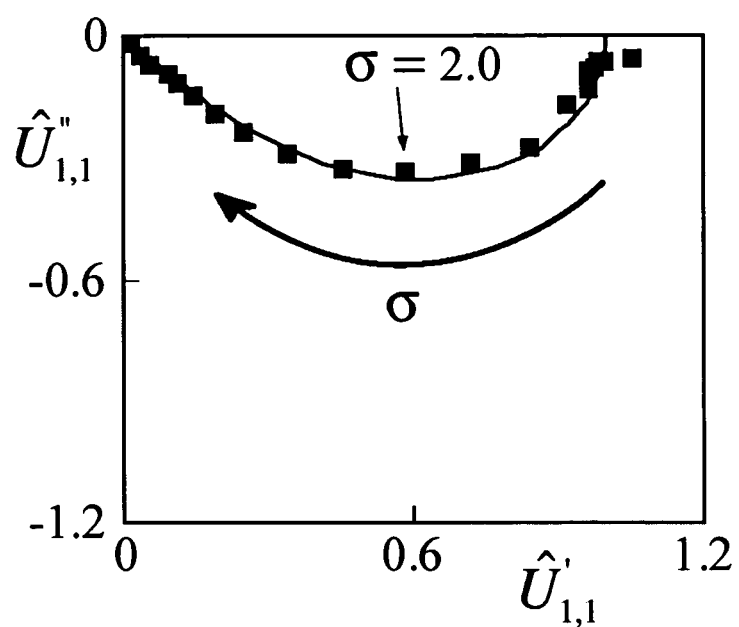
FIG. 36 is a representative Nyquist plot of the measured (symbols) and a model (line) linear response term, $\hat{U}_{1,1}(\sigma)$, of the nondimensionalized amplitude-independent first harmonic overpotential.

FIG. 36 shows that the first order harmonic spectrum (impedance) exhibits the same characteristic Gerischer shape reported previously for LSC-82 on Sm-doped ceria. This behavior has been explained previously using a model found in the literature that assumes an entirely bulk transport reaction pathway. However, questions have remained about the uniqueness of this model vis-à-vis the true mechanism. In order to test this model further, the model has been extended into the nonlinear realm, so as to also compare it to the higher harmonics.

Physical Basis for the Model

The model found in the literature makes the following physical assumptions:
1. The mechanism involves an entirely bulk transport pathway.
2. Resistance to interfacial charge transfer is negligible.
3. The active region of the electrode is significantly smaller than the electrode thickness, but large compared to microstructural features.
4. Gas phase diffusion has no effect on this system.
5. The mixed conductor has high electrical conductivity.

With these assumptions, the porous mixed conductor can be modeled in terms of the 1-D macrohomogeneous conservation of oxygen-ion vacancies in the mixed conductor $$\frac{c_0(1-\varepsilon)}{\tau_S} \frac{\partial x_v}{\partial t} = c_0 \frac{(1-\varepsilon)}{\tau_S} D_v \frac{\partial}{\partial y}\left(A(x_v) \frac{\partial x_v}{\partial y}\right) - 2ar \quad (4a)$$

where $x_v(y,t)$ is the mole fraction of vacant oxygen sites, y is position within the electrode (as measured from the electrode/electrolyte interface), t is time, $\varepsilon$ is the porosity of the electrode, a is the surface area per unit volume, $\tau_S$ is the tortuosity of the solid-state diffusion path in the mixed conductor, $D_v$ is the oxygen vacancy diffusion coefficient, $c_0$ is the concentration of oxygen lattice sites in LSC-82, $A(x_v)$ is a thermodynamic factor (defined below) relating $x_v$ to oxygen activity in the solid, and $r(x_v, P_{O_2}^{gas})$ is the rate of oxygen absorption into the mixed conductor per unit surface area.

The boundary conditions are as follows. At the electrode/electrolyte interface (y=0), the vacancy flux is related to the current perturbation through the oxygen vacancy flux:

$$c_0 \frac{(1-\varepsilon)D_v}{\tau_S} A(x_v) \frac{\partial x_v}{\partial y}\bigg|_{y=0} = \frac{\tilde{i}}{2F} \cos(\tilde{\omega} t) \quad (4b)$$

where $\tilde{i}$ and $\tilde{\omega}$ are the amplitude and frequency of the current perturbation, and F is Faraday's constant. Far away from the electrode/electrolyte interface (y approaches infinity), the vacancy flux approaches zero (equilibrium with the gas phase):

$$\frac{\partial x_v}{\partial y}\bigg|_{y\to\infty} = 0. \quad (4c)$$

Finally, in the absence of interfacial resistances, the electrode overpotential, η, is related to the oxygen vacancy concentration at y=0 through the Nernst equation:

$$\eta = \frac{RT}{4F} \ln \frac{P_{O_2}^{solid}(x_v)\big|_{y=0}}{P_{O_2}^{gas}} \quad (4d)$$

where R is the ideal gas constant, T is the operating temperature of the cell, $P_{O_2}^{solid}$ is the partial pressure of oxygen of the solid, and $P_{O_2}^{gas}$ is the partial pressure of oxygen of the gas.

In extending this model into the nonlinear realm, Equations (4a-d) reveal two significant sources of nonlinearity. The first arises from the thermodynamic relationship between $P_{O_2}^{solid}$ and the nonstoichiometry ($\delta=3x_v$) in $La_{1-x}Sr_xCoO_{3-\delta}$. This relationship can be calculated by fitting measured nonstoichiometry values to a modification of Lankhorst's thermodynamic model taken from the literature, for which $P_{O_2}^{solid}(x_v)$ and $A(x_v)$ can be expressed as:

$$A(x_v) = -\frac{1}{2}\frac{\partial \ln P_{O_2}^{solid}(x_v)}{\partial \ln x_v} = A_0\left(1 + B\left(\frac{x_v}{x_v^0} - 1\right)\right) \quad (4e)$$

where $x_v^0$ and $A_0$ are the values of $x_v$ and A at equilibrium with the gaseous $P_{O_2}$, and $B=1-1/A_0$. The values of $x_v^0$, $A_0$, and B at 750° C. in air were extracted in this case from measurements of oxygen nonstoichiometry of LSC-82 versus $P_{O_2}$ and T taken from the literature, and found to be $x_v^0=0.0021$, $A_0=1.19$, and $B=0.16$.

The second source of nonlinear behavior arises from the rate of oxygen exchange at the gas-solid interface, $r(x_v, P_{O_2}^{gas})$. Since no consensus has been established as to the specific kinetics governing this reaction, a semi-empirical rate expression was employed based on non-equilibrium thermodynamics that considers the oxygen chemical potential difference between the gas and the solid bulk as the driving force for the reaction:

$$r = nk\left(P_{O_2}^{gas}\right)^p \frac{(1-\exp(-\Delta/RT))}{\exp(-(q-p)\Delta/RT)} \quad (4f)$$

where $\Delta=(RT/n)(\log(P_{O_2}^{gas})-\log(P_{O_2}^{solid}))$, k is a kinetic rate constant, and n, p, and q are kinetic parameters that depend on the specific kinetic steps on the surface, assuming one is rate-limiting.

Governing Equations—Dimensionless Form

The model in Equations (4a)-(4f) invokes a large number of physical properties (e.g., diffusion coefficient, porosity, tortuosity, etc.), many of which have counterbalancing effects on the system. In order to simplify the solution of the model, these equations were cast in dimensionless form, allowing many of the parameters to be grouped into a limited set of unique parameters. Table 1 below summarizes each dimensional variable, its relationship to its dimensionless form, and the characteristic dimensional parameters arising from the nondimensionalization. These parameters include a characteristic length, y*, describing the size of the active region of the electrode under steady-state conditions, a characteristic time constant, t*, describing the response frequency of the electrode, a characteristic current, i*, describing the magnitude of current density at which the system becomes significantly nonlinear, and a characteristic overpotential η* describing the magnitude of the response to a current perturbation of magnitude i*. The parameters y*, t*, and (η*/i*) have the same meaning as the parameters $l_\delta$, $t_{chem}$, and $R_{chem}$, respectively, as described previously in the literature. With the definitions in Table 1, Equations (4a)-(4f) become:

$$\frac{\partial X}{\partial \tau} = \frac{\partial}{\partial \xi}\left((1+BX)\frac{\partial X}{\partial \xi}\right) - \frac{n}{2A_0}\frac{\left(1-\exp\left(-\frac{2A_0}{n}\lambda\right)\right)}{\exp(-2A_0(q-p)\lambda)}, \quad (5a)$$

with boundary conditions:

$$(1+BX)\frac{\partial X}{\partial \xi}\bigg|_{\xi=0} = \alpha\cos(\sigma\tau), \quad \frac{\partial X}{\partial \xi}\bigg|_{\xi\to\infty} = 0, \quad (5b)$$

where $\lambda = BX + (1-B)\ln(1+X)$ and:

$$U = -\lambda|_{\xi=0}. \quad (5c)$$

Frequency Domain Formulation

The steady periodic solution to Equation 5 is obtained by first expanding the dimensionless concentration, $X(\xi, \tau, \alpha, \sigma)$, into a discrete complex Fourier series:

$$X(\xi, \tau, \alpha, \sigma) = \quad (6a)$$
$$\frac{1}{2}\sum_{k=0}^{\infty}\left(\hat{X}_k(\xi, \alpha, \sigma)\exp(jk\sigma\tau) + \hat{X}_{-k}(\xi, \alpha, \sigma)\exp(jk\sigma\tau)\right),$$

where the time-independent complex coefficients $\hat{X}_{\pm k}(\xi,\alpha,\sigma)$ can be written in terms of real and imaginary components $\hat{X}_{\pm k}=\hat{X}'_k \pm j\hat{X}''_k$. The amplitude dependence of each complex Fourier coefficient can then be expressed by expanding $\hat{X}_{\pm k}(\xi,\alpha,\sigma)$ in a regular perturbation series of alternating powers of α:

$$\hat{X}_{\pm k}(\xi, \alpha, \sigma) = \sum_{r=1}^{\infty}\alpha^{k+2r-2}\hat{X}_{k,k+2r-2}(\xi, \sigma) \quad (6b)$$

where $\hat{X}_{k,m}(\xi,\sigma)$ represents the magnitude and phase of vacancy concentration modulations occurring at frequency kσ, of order $\alpha^m$ in perturbation amplitude.

By substituting the definitions in Equations (6a) and (6b) into Equations (5a) and (5b), a series of ordinary differential equations (and boundary conditions) for each term $\hat{X}_{k,m}(\xi,\sigma)$ of increasing order in k and m is obtained. Although these equations are coupled, equations of a particular order in k and m only depend on lower order terms, and thus the series of equations can be solved sequentially beginning with the steady-state solution, $\hat{X}_0(\xi,\alpha,\sigma)$, and proceeding upward in values of k and m (see Numerical Analysis section below).

After solving for the concentration, the overpotential harmonics are calculated by first expanding $U(\tau, \alpha, \sigma)$ into harmonic terms $\hat{U}_{k,m}(\sigma)$ in a similar manner as Equation (6). Upon substitution of this expansion into Equation (5c), a series of algebraic equations are obtained relating each overpotential harmonic $\hat{U}_{k,m}(\sigma)$ to the concentration coefficients $\hat{X}_{k,m}(\eta,\sigma)|_{\xi=0}$.

Numerical Analysis

A combination of computer software tools were used to obtain a solution to the system of equations described above. Mathematica (Wolfram Research) was first used to derive (analytically) the equation coefficients entering the ordinary differential equations and boundary conditions describing $\hat{X}_{k,m}(\xi,\sigma)$ and the equations relating $\hat{U}_{k,m}(\sigma)$ to $\hat{X}_{k,m}(\xi,\sigma)|_{\eta=0}$. For this system, it was experimentally difficult to measure harmonics above the third harmonic (k=3); therefore, this series was truncated at k=m=3, leaving five sets of ordinary differential equations and boundary conditions for $\hat{X}_{0,0}(\eta,\sigma)$, $\hat{X}_{0,2}(\eta,\sigma)$, $\hat{X}_{1,1}(\eta,\sigma)$, $\hat{X}_{1,3}(\eta,\sigma)$, and $\hat{X}_{3,3}(\eta,\sigma)$, and five equations relating $\hat{U}_{k,m}(\sigma)$ to $\hat{X}_{k,m}(\eta,\sigma)|_{\eta=0}$. Error due to truncation is expected to be of order $\alpha^4$.

These equations were input into FEMLAB (ComsolAB), a finite element package for use with MATLAB (The Mathworks, Inc.). For each simulation, 67 grid nodes were used in the spatial domain. This example focuses on the behavior at electrode/electrolyte interface; therefore a higher concentration of nodes is needed near an interface. The grid points are distributed in MATLAB by an expression that provides zero length elements at the origin, that quickly increase in size as they depart from the origin.

Results/Discussion

Since many of the parameters entering the model described above are unknown or poorly characterized, it is difficult to compare the experimental data to the model directly on a dimensional basis. As an alternative, the data can be non-dimensionalize and compared to the model in dimensionless form. To accomplish this, a value of i* was established and used to determine the voltage harmonics of the cell, $\hat{V}_{k,m}(\tilde{\omega})$, as described in Equation (3) and FIG. 36. The voltage harmonics were then converted into overpotential harmonics, $\hat{\eta}_{k,m}(\tilde{\omega})$, by subtracting the Ohmic contribution of the electrolyte, $$R_e = \lim_{\tilde{\omega} \to \infty} (d\hat{V}_1 / d\tilde{i}),$$

and dividing by 2 (since the odd voltage harmonics contain contributions from both electrodes):

$\hat{\eta}_{1,1}(\tilde{\omega}) = (\hat{V}_{1,1}(\tilde{\omega}) - R_e i^*)/2$ $\hat{\eta}_{1,3}(\tilde{\omega}) = \hat{V}_{1,3}(\tilde{\omega})/2$ $\hat{\eta}_{3,3}(\tilde{\omega}) = \hat{V}_{3,3}(\tilde{\omega})/2$ (7)

The data pairs of $(\hat{\eta}_{k,m}, \tilde{\omega})$ were then multiplied by $(1/\eta^*, t^*)$ to convert to $(\hat{U}_{k,m}, \sigma)$, as defined in Table 1.

Non-dimensionalization of the data (as described above) requires knowing the values of three dimensional parameters i*, $\eta^*$, and t*. Although $\eta^*$ is well defined in terms of $A_0$ ($\eta^*=52$ mV at 750° C.), i* and t* are not known in advance. Therefore, the first harmonic cell voltage was fit to a Gerischer impedance in the limit of low perturbation amplitude:

$$\lim_{\tilde{i} \to 0} \frac{d\hat{V}_1(\tilde{i},\tilde{\omega})}{d\tilde{i}} = R_e + \frac{2\eta^*/i^*}{(\sqrt{1+j\tilde{\omega}t^*})^*}, \quad (8)$$

yielding values of i*=70 mA and t*=31 seconds. These values were then used to nondimensionalize the remaining higher-harmonic data, as described above.

FIG. 36 compares $\hat{U}_{1,1}(\sigma)$ calculated from the experimental first harmonic data to that predicted by the model. Although the agreement between model and data is reasonable, this result merely confirms that the model can be made to fit the first harmonic data with appropriate values of the Gerischer parameters t* and $\eta^*/i^*$. This result holds true regardless of the values of the other parameters governing the system, including the nonlinear thermodynamic and kinetics parameters $A_0$, B, n, q, and p. Thus the first harmonic (impedance) reveals little or nothing about the values of these other parameters. Rather, it merely establishes a frequency and magnitude reference for the other harmonics (through the values of i* and t*).

Figure 37:
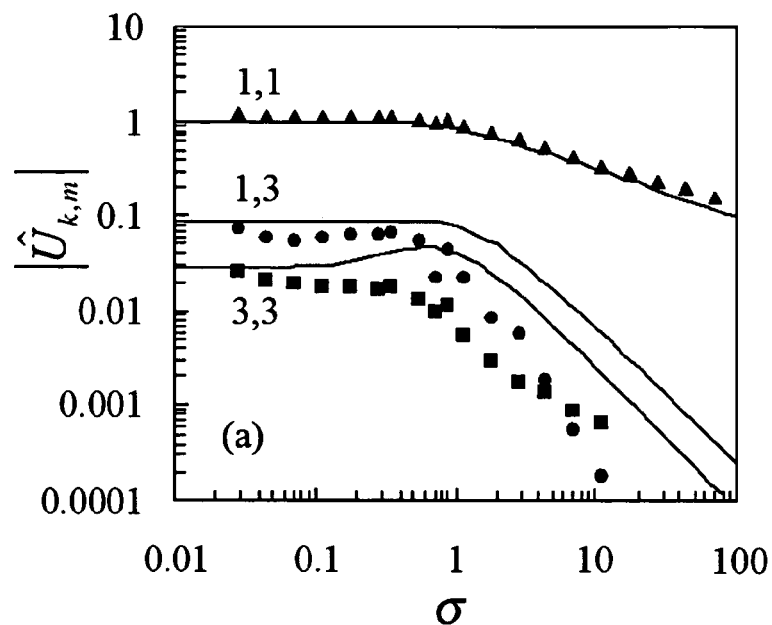
FIG. 37 illustrates representative Bode plots of the measured (symbols) and model values (line) of amplitude-independent Fourier coefficients of the nondimensionalized overpotential magnitude values for various harmonics, including $\hat{U}_{1,1}(\sigma)$ (triangles), $\hat{U}_{1,3}(\sigma)$ (squares), $\hat{U}_{3,3}(\sigma)$ (circles), wherein the model assumes that the thermodynamic properties are those of bulk LSC-82, and that the oxygen absorption kinetics are described by Equation 9.
Figure 38:
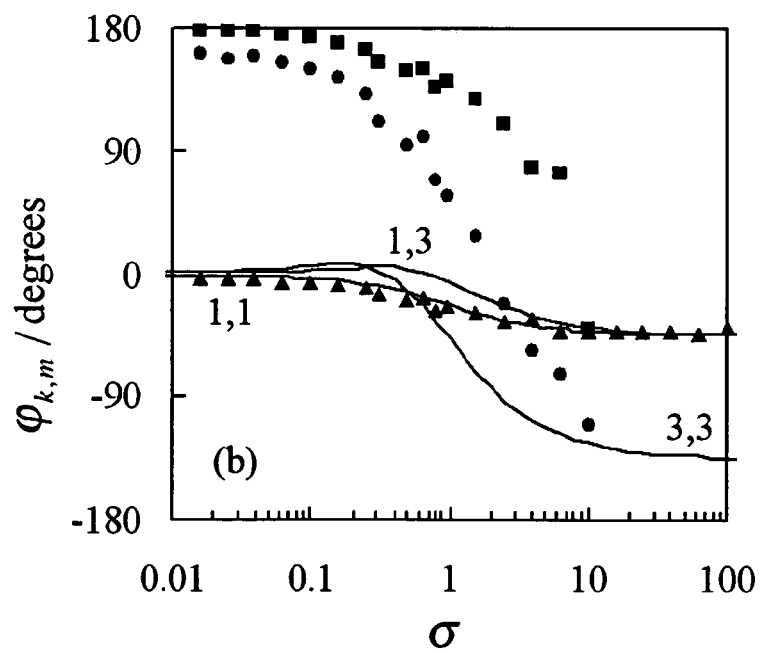
FIG. 38 illustrates representative Bode plots of the measured (symbols) and model values (line) of amplitude-independent Fourier coefficients of the nondimensionalized overpotential phase values for various harmonics, including $\hat{U}_{1,1}(\sigma)$ (triangles), $\hat{U}_{1,3}(\sigma)$ (squares), $\hat{U}_{3,3}(\sigma)$ (circles), wherein the model assumes that the thermodynamic properties are those of bulk LSC-82, and that the oxygen absorption kinetics are described by Equation 9.

Extending this comparison to the higher harmonics, FIGS. 37-42 show the magnitude and phase of $\hat{U}_{1,1}(\sigma)$, $\hat{U}_{1,3}(\sigma)$, and $\hat{U}_{3,3}(\sigma)$ compared to the model assuming various values for the parameters $A_0$, B, n, q, and p. In FIGS. 37 and 38, the model assumes values of $x_v^0=0.0021$, $A_0=1.19$, and B=0.16, as determined experimentally for bulk LSC-82. The kinetic constants were assumed to be n=1, q=1, and p=0.5, which correspond to the following rate expression for the oxygen absorption kinetics:

$$r = k\left(\frac{P_{O_2}^{gas}}{(P_{O_2}^{solid})^{1/2}} - (P_{O_2}^{solid})^{1/2}\right) \quad (9)$$

This expression assumes that absorption kinetics are first-order in gas-phase $P_{O_2}$, but the exchange rate at equilibrium is half-order in $P_{O_2}$. Experimental results for component $\hat{U}_{1,1}$ show good agreement with theory (by definition), however $\hat{U}_{1,3}$ and $\hat{U}_{3,3}$ show poor agreement with theory, both in magnitude and phase. The signs of $\hat{U}_{1,3}$ and $\hat{U}_{3,3}$ are negative at low frequency (phase of 180°), while the model predicts positive values (phase of 0°). The magnitudes of $\hat{U}_{1,3}$ and $\hat{U}_{3,3}$ are also in poor agreement with the model throughout the frequency spectrum, exhibiting a characteristic transition frequency much lower than predicted by the model based on the first harmonic. Finally, the divergent phase behavior of $\hat{U}_{1,3}$ and $\hat{U}_{3,3}$ predicted by the model at high frequency, is absent in the data.

Figure 39:
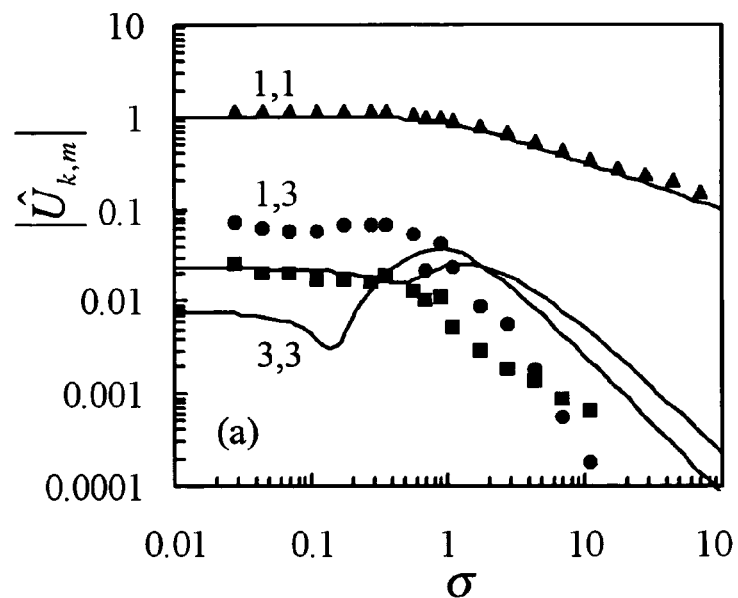
FIG. 39 illustrates representative Bode plots of the measured (symbols) and model values (line) of amplitude-independent Fourier coefficients of the nondimensionalized overpotential magnitude values of various harmonics, including $\hat{U}_{1,1}(\sigma)$ (triangles), $\hat{U}_{1,3}(\sigma)$ (squares), $\hat{U}_{3,3}(\sigma)$ (circles), wherein the model assumes that the thermodynamic properties are those of bulk LSC-82, and that the oxygen absorption kinetics are described by Equation 10.
Figure 40:
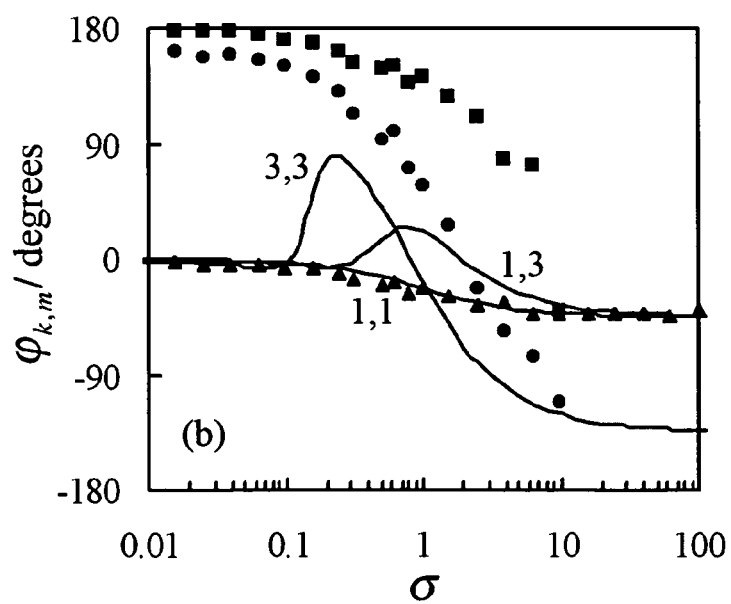
FIG. 40 illustrate representative Bode plots of the measured (symbols) and model values (line) of amplitude-independent Fourier coefficients of the nondimensionalized overpotential phase values of various harmonics, including $\hat{U}_{1,1}(\sigma)$ (triangles), $\hat{U}_{1,3}(\sigma)$ (squares), $\hat{U}_{3,3}(\sigma)$ (circles), wherein the model assumes that the thermodynamic properties are those of bulk LSC-82, and that the oxygen absorption kinetics are described by Equation 10.

Based on the hypothesis that the disparity shown in FIGS. 37 and 38 is a result of incorrect assumptions about the absorption mechanism (Equation (9)), a variety of other absorption rate expressions were considered. For example, FIGS. 39 and 40 compare the experimental data and model assuming n=2, q=0.5, and p=0.5, which corresponds to another (commonly assumed) rate expression for the absorption kinetics:

$$r = k\left((P_{O_2}^{gas})^{1/2} - (P_{O_2}^{solid})^{1/2}\right), \quad (10)$$

which assumes exchange kinetics at equilibrium are half-order in $P_{O_2}$ but treats the reaction as entirely symmetric. Since this model is degenerate in the first harmonic with that in FIGS. 37 and 38, the measured value of $\hat{U}_{1,1}$ shows equally good (identical) agreement with theory. However, the higher harmonic spectra $\hat{U}_{1,3}$ and $\hat{U}_{3,3}$ predicted by the model again show poor agreement, including incorrect phase (sign), and the presence of harmonic "nullifications" caused by sudden sign changes associated with destructive interactions among oscillating harmonics, not observed in the experimental data.

A variety of other rate expressions were considered, varying parameters n, p, and q, corresponding to different assumptions about the rate-limiting step, the reaction orders in the forward and backward direction, and the dependence of the exchange kinetics on $P_{O_2}$ at equilibrium. However, none of these rate expressions were found to be consistent with the higher harmonic data. Abandoning any particular exchange mechanism, and instead varying n, p, and q empirically, moderate agreement was found for q=1, p=0.07, and n=0.41. However, these values are inconsistent with the strong $P_{O_2}$ dependence of the equilibrium oxygen exchange rate (p≥0.25) observed in the literature. In addition, these parameters correspond to oxygen desorption being proportional to $(P_{O_2}^{gas})^{+1.4}$, which is difficult to rationalize based on any realistic exchange mechanism. Thus, the results shown in FIGS. 37-40 suggest that for LSC-82 on SDC at 750° C. in air, the measured higher harmonics cannot be explained in terms of an entirely bulk transport path, assuming the thermodynamic properties of bulk LSC-82.

Figure 41:
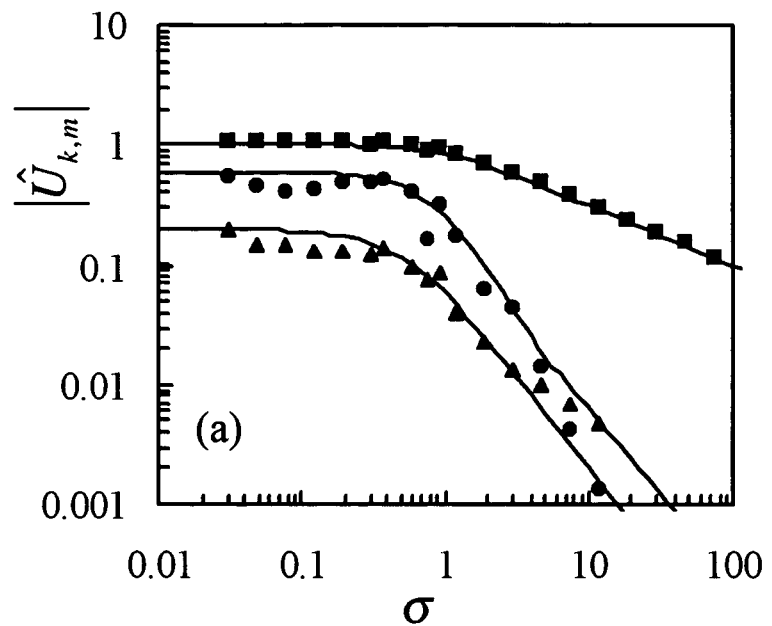
FIG. 41 illustrates representative Bode plots of the measured (symbols) and model values (line) of amplitude-independent Fourier coefficients of the nondimensionalized overpotential magnitude values of various harmonics, including $\hat{U}_{1,1}(\sigma)$ (triangles), $\hat{U}_{1,3}(\sigma)$ (squares), $\hat{U}_{3,3}(\sigma)$ (circles), wherein the model assumes that the thermodynamic properties are those of bulk $La_{0.43}Sr_{0.57}CoO_{3-\delta}$ and that the oxygen absorption kinetics are described by Equation 9.
Figure 42:
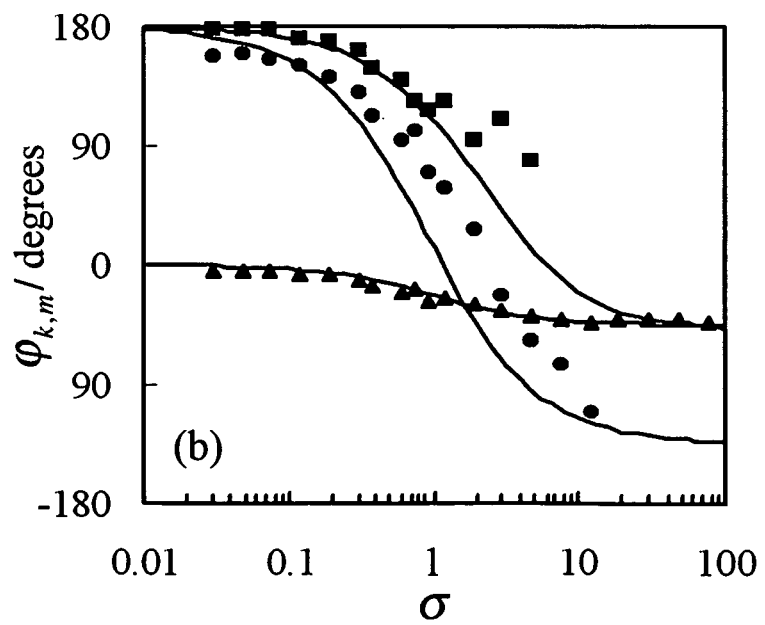
FIG. 42 illustrates representative Bode plots of the measured (symbols) and model values (line) of amplitude-independent Fourier coefficients of the nondimensionalized overpotential phase values of various harmonics, including $\hat{U}_{1,1}(\sigma)$ (triangles), $\hat{U}_{1,3}(\sigma)$ (squares), $\hat{U}_{3,3}(\sigma)$ (circles), wherein the model assumes that the thermodynamic properties are those of bulk $La_{0.43}Sr_{0.57}CoO_{3-\delta}$ and that the oxygen absorption kinetics are described by Equation 9.

In order to gain some insight about what other mechanisms might be governing the electrode, other sources of nonlinearity in the system were considered. For example, FIGS. 41 and 42 compare the experimental and theoretical values of $\hat{U}_{k,m}$ assuming the reaction kinetics of Equation (9) but where the values of $x_v^0$, $A_0$, and B are taken to be those of bulk $La_{0.43}Sr_{0.57}CoO_{3-\delta}$, a material with a much higher vacancy concentration than LSC-82 under the same conditions. In this case the value of i* calculated from the first harmonic is 293 mA. As evidenced by the agreement between measured and calculated harmonic spectra $\hat{U}_{1,3}$ and $\hat{U}_{3,3}$, the nonlinear characteristics of the LSC-82 electrode would appear to be more consistent with the bulk thermodynamic properties of $La_{0.43}Sr_{0.57}CoO_{3-\delta}$ than those of LSC-82.

Several reports demonstrate that thermodynamic properties of nanocrystalline or thin film ceramics can deviate in value from their bulk thermodynamic properties. Specifically, the literature has shown that the thermodynamic properties of a thin film of $La_{0.6}Sr_{0.4}CoO_{3-\delta}$ (LSC-64) on SDC, while qualitatively similar to the bulk properties of LSC-64, are more consistent with a material having a much higher enthalpy of vacancy formation. Thus, the thin film exhibits a much lower vacancy concentration than predicted based on the bulk properties of LSC-64. One possible interpretation of FIGS. 41 and 42 is that for related (but opposite) reasons, the vacancy concentration of LSC-82 in a porous electrode near the SDC interface is higher than that for bulk LSC-82.

However, the results shown in FIGS. 41 and 42 should not be interpreted too literally. There are two factors that appear to contradict the interpretation described above. First, the literature reports a decrease, not an increase, in the vacancy concentration for the thin film relative to the bulk. Secondly, one likely cause of the effects observed is that changes in lattice volume near the interface are constrained by adherence to the SDC substrate, resulting in stresses that may alter the oxygen exchange enthalpy. The same level of lattice stress is not expected in a thick porous film, particularly at the higher temperatures under study.

An alternative interpretation of FIGS. 41 and 42 is that the electrode operates via a mixed bulk and surface path, but that the apparent "thermodynamic properties of the surface" (while similar to the bulk qualitatively) involves a much higher "surface vacancy concentration" than in the bulk. This hypothesis is consistent with some atomistic simulations, which suggest that defect energies at the surface are lower than in the bulk, leading toward segregation of strontium ions to the surface of the perovskite. Possible experimental evidence for this effect includes X-ray photo-electron spectroscopy measurements of $La_{1-x}Sr_xMO_{3-\delta}$ which suggest that the strontium content of the surface is enriched relative to the bulk.

Conclusions

This example describes a method to quantify the nonlinear response of an electrochemical system by measuring higher-order voltage harmonics generated by moderate-amplitude sinusoidal current perturbations. The method involves direct digital acquisition of the response signal, followed by time apodization and Fourier transformation of the data into the frequency domain, where the magnitude and phase of each harmonic signal can be readily quantified. A framework for predicting the higher harmonics based on a particular physical model was described.

For the case of porous $La_{0.8}Sr_{0.2}CoO_{3-\delta}$ electrodes on Sm-doped ceria (SDC) at 750° C. in air, the third-order harmonic spectra $\hat{V}_{1,3}(\omega)$ and $\hat{V}_{3,3}(\omega)$ were found to exhibit distinctive features that could be used to distinguish various possible mechanisms that are degenerate in the first harmonic (impedance). Assuming oxygen reduction is co-limited by oxygen absorption and transport in the bulk of the mixed conductor, the measured harmonics were compared to those predicted for various scenarios for the oxygen absorption kinetics. This comparison shows that the measured harmonics are inconsistent with any realistic model for the absorption kinetics, assuming an entirely bulk-transport pathway. The data were found to be more consistent with a variation of this model that assumes oxygen absorption is governed by dissociative adsorption, but the thermodynamic properties of the electrode material are assumed to be that of bulk $La_{0.43}Sr_{0.57}CoO_{3-\delta}$. One possible interpretation of this result is that the electrode operates by parallel surface and bulk paths, where the apparent concentration of mobile vacancies on the surface is much higher than in the bulk.

TABLE 1

RELATIONSHIP BETWEEN DIMENSIONAL VARIABLES AND THEIR NONDIMENSIONAL FORM

| Quantity | Dimensional Variable | Dimensionless Form | Relationship | Dimensional Group |
|---|---|---|---|---|
| Time | t | τ | $\tau = \dfrac{t}{t^*}$ | $t^* = \dfrac{c_0 x_v^0 (1-\varepsilon)}{4ak(P_{O_2}^{gas})^p}$ |
| Position | y | ξ | $\xi = \dfrac{y}{y^*}$ | $y^* = \sqrt{\dfrac{c_0 x_v^0 D_v (1-\varepsilon)}{4ak(P_{O_2}^{gas})^p \tau_s}}$ |
| Concentration | $x_v$ | X | $X = \dfrac{x_v - x_v^0}{x_v^0}$ | $x_v^0$ |

TABLE 1-continued

RELATIONSHIP BETWEEN DIMENSIONAL VARIABLES AND THEIR NONDIMENSIONAL FORM

| Quantity | Dimensional Variable | Dimensionless Form | Relationship | Dimensional Group |
|---|---|---|---|---|
| Overpotential | $\hat{\eta}$ | $\hat{U}$ | $\hat{U} = \dfrac{\hat{\eta}}{\eta^*}$ | $\eta^* = \dfrac{A_0 RT}{2F}$ |
| Current | $\tilde{i}$ | $\alpha$ | $\alpha = \dfrac{\tilde{i}}{i^*}$ | $i^* = 2FA_0 \sqrt{\dfrac{4ak(P_{O_2}^{gas})^p c_0 x_v^0 D_v (1-\varepsilon) A_0}{\tau_s}}$ |
| Frequency | $\hat{\omega}$ | $\sigma$ | $\sigma = \hat{\omega} t^*$ | $t^* = \dfrac{c_0 x_v^0 D_v (1-\varepsilon)}{4ak(P_{O_2}^{gas})^p}$ |

NOMENCLATURE USED IN THIS APPLICATION

Arabic a specific surface area of the electrode, $cm^2/cm^3$
A thermodynamic factor relating $x_v$ to oxygen activity in the solid (dimensionless)
$A_0$ value of A at equilibrium with the gas phase (dimensionless)
b Gaussian apodization parameter (cycles)
B $1-1/A_0$ (dimensionless)
$c_0$ concentration of oxygen lattice sites (mol/cm³)
$D_v$ Oxygen vacancy diffusion coefficient (cm²/sec)
F Faraday's constant (96,487 C./mol)
i current density (A/cm²)
$\tilde{i}$ amplitude of the current perturbation (A/cm²)
i* characteristic current density describing the electrode response (A/cm²)
j imaginary unity, $j=\sqrt{-1}$ (dimensionless)
k kinetic rate constant governing oxygen exchange (mol/cm²/s) (k also used as index)
n kinetic parameter governing oxygen exchange (dimensionless)
p kinetic parameter governing oxygen exchange (dimensionless)
$P_{O_2}^{gas}$ partial pressure of oxygen in the gas (atm)
$P_{O_2}^{solid}$ fugacity (thermodynamic $P_{O_2}$) of oxygen in the solid (atm)
q kinetic parameter governing oxygen exchange (dimensionless)
r rate of oxygen absorption from the gas into the mixed conductor (mol $O_2$/cm²/s)
R ideal gas constant (8.314 J/mol-K)
$R_e$ area-specific ohmic resistance of the electrolyte (ohm-cm²)
t time (s)
t* characteristic time constant describing the response rate of the electrode (s)
T temperature (K)
U nondimensionalized electrode overpotential (dimensionless)
V cell voltage (volts)
W Gaussian apodization window (dimensionless)
$x_v$ mole fraction of oxygen vacancies $x_v=\delta/3$ (dimensionless)
$x_v^0$ mole fraction of oxygen vacancies at equilibrium with the gas (dimensionless)
X nondimensionalized vacancy concentration (dimensionless)
y position within the electrode (cm)
y* characteristic length describing the active region of the electrode (cm)
Z area-specific impedance (ohm-cm²)

Greek $\alpha$ nondimensionalized current perturbation amplitude (dimensionless)
$\delta$ oxygen nonstoichiometry of the electrode material ABO_ (dimensionless)
$\Delta$ thermodynamic driving force for oxygen absorption (J/mol/K)
$\varepsilon$ porosity of the electrode (dimensionless)
$\eta$ electrode overpotential (volts)
$\eta^*$ characteristic voltage describing the electrode response (volts)
$\lambda$ nondimensionalized driving force for oxygen absorption (dimensionless)
$\sigma$ nondimensionalized current perturbation frequency (dimensionless)
$\tau$ nondimensionalized time (dimensionless)
$\tau_S$ torturosity of the solid-state diffusion path in the mixed conductor (dimensionless)
$\xi$ nondimensionalized position (dimensionless)
$\omega$ radial frequency ($s^{-1}$)
$\hat{\omega}$ radial frequency of the current perturbation ($s^{-1}$)
Guide to Transform Variables and Indices
V(t) time dependent variable
$\hat{V}(\omega)$ Fourier transform of V(t)
$\hat{V}_k$ Fourier coefficient of the $k^{th}$ harmonic contribution to $\hat{V}(\omega)$
$\hat{V}_{-k}$ complex conjugate of $\hat{V}_k$
$\hat{V}'_k$ real part of $\hat{V}_k$
$\hat{V}''_k$ imaginary part of $\hat{V}_k$
$\hat{V}_{k,m}$ $m^{th}$ order dependence of $\hat{V}_k$ on perturbation amplitude While embodiments have been illustrated and described, it will be appreciated that various changes can be made therein without departing from the spirit and scope of the invention.

The embodiments of the invention in which an exclusive property or privilege is claimed are defined as follows:

1. A method for performing nonlinear electrochemical impedance spectroscopy, comprising:
   conducting nonlinear electrochemical impedance spectroscopy on an electrochemical system to be analyzed with a system comprising: a function generator, a potentiostat or galvanostat, and one or more computers, wherein the electrochemical system is analyzed by the method comprising:
- (a) generating electrical perturbation signals with the function generator;
- (b) applying the electrical perturbation signals generated by the function generator to the electrochemical system and maintaining a voltage difference or current difference across the electrochemical system with the potentiostat or galvanostat;
- (c) measuring electrical response signals of the electrochemical system;
- (d) with the one or more computers, calculating an amplitude-independent harmonic structure from the signals obtained in response to the application to the electrochemical system of the perturbation signals having a perturbation amplitude and a perturbation frequency, wherein the perturbation signals include a sampling in a range of the perturbation amplitudes proportional to a characteristic value of the electrochemical system, and a sampling over a range of perturbation frequencies that include sampling in a range of frequencies proportional to a characteristic value of the electrochemical system;
- (e) with the one or more computers, determining the perturbation signals that are of moderate amplitude by plotting a real and imaginary part of a higher order harmonic versus the perturbation amplitude raised to a power the same as the order of the harmonic;
- (f) when the plot is not substantially linear, changing the perturbation amplitude and repeating step (e);
- (g) when the plot is substantially linear, with the one or more computers, deriving the amplitude-independent harmonic structure comprising at least one higher order harmonic greater than one using response signals sampled when the perturbation signals are of moderate amplitude; and
- (h) with the one or more computers, identifying, from a library of standard harmonic data, a model that matches the harmonic structure and characterizing a rate-limiting electrochemical process of the electrochemical system.

2. The method of claim 1, comprising providing a different range of perturbation amplitudes for each harmonic that is proportional to the characteristic value of the electrochemical system, and the range of perturbation amplitudes for each harmonic is defined, at least, by response signals for which a fit of the response signal values to the perturbation signal values to the power of the same order includes a substantially linear portion.

3. The method of claim 2, wherein the fit of the response signal values to the perturbation signal values is resolvable by a finite power series less than 4 terms.

4. The method of claim 1, wherein a fit of the response signal values to the perturbation signal values is resolvable by a finite power series less than 4 terms.

5. The method of claim 1, comprising expressing nonlinear harmonics as a power series, wherein each individual harmonic term in the power series will yield an amplitude-independent harmonic structure when plotted with respect to the perturbation frequency.

6. The method of claim 1, comprising providing a different range of perturbation amplitudes for each harmonic contribution that is proportional to the characteristic value of the electrochemical system, and the range of sampling is selected to be the narrowest range from the ranges of every harmonic probed.

7. The method of claim 1, wherein the characteristic value is current or voltage.

8. The method of claim 1, comprising providing a harmonic structure that includes one or more harmonic contributions of higher order greater than one and the harmonic contributions of higher orders that are resonant with the one or more harmonic contributions.

9. The method of claim 1, wherein a stable response of the electrochemical system obeys the following equations:

$$X(t, x, \tilde{\omega}) = X_0(x, \tilde{\omega}) + \frac{1}{2}\sum_{m=1}^{\infty}\left(\hat{X}_m(x, \tilde{\omega})e^{jm\tilde{\omega}t}\right) + \frac{1}{2}\sum_{m=1}^{\infty}\left(\hat{X}_{-m}(x, \tilde{\omega})e^{-jm\tilde{\omega}t}\right)$$

where $$\hat{X}_0 = X'_0,$$
$$\hat{X}_m = X'_m + jX''_m,$$
$$\hat{X}_{-m} = X'_m - jX''_m,$$
$$X'_m(x, \tilde{\omega}) = \sum_{r=1}^{\infty} i^{m+2r-2} X'_{m,m+2r-2}(\tilde{\omega}), \text{ and}$$
$$X''_m(x, \tilde{\omega}) = \sum_{r=1}^{\infty} i^{m+2r-2} X''_{m,m+2r-2}(\tilde{\omega}); \text{ wherein}$$

X=Voltage or current response
T=Time
$\tilde{x}$=Current or voltage perturbation amplitude
$\tilde{\omega}$=Perturbation frequency
m=Harmonic index
j=Imaginary unity, $(-1)^{1/2}$
$X'_m$=Real part of the complex Fourier coefficient of the mth harmonic
$X''_m$=Imaginary part of the complex Fourier coefficient of the mth harmonic
$X'_{m,p}$=Real part of pth contribution to the mth harmonic (p=m+2r−2)
$X''_{m,p}$=Imaginary part of pth contribution to the mth harmonic (p=m+2r−2)
provided, that when X=V, x=i; and if X=I, x=V.

10. The method of claim 1, further comprising scaling the perturbation amplitude in accordance with the measured impedance of the electrochemical system as a function of frequency.

11. The method of claim 1, further comprising:
- (i) obtaining current and voltage signals as a function of time;
- (j) removing biases in the data to obtain unbiased data;
- (k) applying an apodization technique to the unbiased data to obtain apodized data;
- (l) converting the apodized data to the frequency domain using a complex fast Fourier transform technique to obtain transformed data in the frequency domain;
- (m) generating an equation representing time domain signals as a linear superposition of steady periodic harmonics of unknown amplitude and phase;
- (n) solving the equation generated in step (e) to obtain a general frequency domain equation comprising real and imaginary harmonic terms;
- (o) fitting the real and imaginary harmonic terms of the data in the frequency domain to the general frequency domain equation using a data fitting technique;

(p) recovering the real and imaginary term of each harmonic from the fit of the data in step (o);

(q) multiplying each real and imaginary term of each harmonic by a phase correction to establish the absolute phase of each real and imaginary term relative to the current perturbation; and (r) expressing the nonlinear dependence of the harmonics as a power series, wherein each individual harmonic term in the power series will yield an amplitude-independent harmonic structure when plotted with respect to the perturbation frequency.

12. The method of claim 11, wherein the data fitting technique is a linear least-squares data fitting technique.

13. A system for performing nonlinear electrochemical impedance spectroscopy, comprising:

a function generator configured to generate an electrical alternating sinusoidal voltage or current signal having a predetermined amplitude and a predetermined frequency;

a digitizer;

a potentiostat or galvanostat in communication with the function generator and digitizer, wherein the potentiostat is configured to maintain a voltage difference across an electrochemical system or the galvanostat is configured to maintain a current across an electrochemical system; and a computer in communication with the function generator, the computer having a central processing unit and storage medium, wherein the computer is programmed to perform steps comprising:

(a) commanding the function generator to generate the electrical perturbation signals that are applied to an electrochemical system via the potentiostat or galvanostat;

(b) recording electrical response signals of the electrochemical system, wherein the signals have been digitized by the digitizer;

(c) calculating an amplitude-independent harmonic structure from signals obtained in response to the application to an electrochemical system of perturbation signals having a perturbation amplitude and a perturbation frequency, wherein the perturbation signals include a sampling in a range of the perturbation amplitudes proportional to a characteristic value of the electrochemical system;

(d) determining the perturbation signals that are of moderate amplitude by plotting a real and imaginary part of a higher order harmonic versus the perturbation amplitude raised to a power the same as the order of the harmonic;

(e) when the plot is not substantially linear, changing the perturbation amplitude and repeating step (d);

(f) when the plot is substantially linear, deriving the amplitude-independent harmonic structure comprising at least one higher order harmonic greater than one using system response signals sampled when the perturbation signals are of moderate amplitude; and (g) identifying from a library of standard harmonic data, a model that matches the harmonic structure to characterize a rate-limiting electrochemical process of the electrochemical system.

14. A method for performing nonlinear electrochemical impedance spectroscopy, comprising:

conducting nonlinear electrochemical impedance spectroscopy on an electrochemical system to be analyzed with a system comprising: a function generator, a potentiostat or galvanostat, and a computer, wherein the electrochemical system is analyzed by the method comprising:

(a) generating electrical perturbation signals with the function generator;

(b) applying the electrical perturbation signals generated by the function generator to the electrochemical system and maintaining a voltage difference or current difference across the electrochemical system with the potentiostat or galvanostat;

(c) measuring electrical response signals of the electrochemical system;

(d) with the computer, calculating an amplitude-independent harmonic structure from the signals obtained in response to the application to the electrochemical system of the perturbation signals having a perturbation amplitude and a perturbation frequency, wherein a fit of response signal values to the perturbation signal values is resolvable by a finite power series;

(e) with the computer, determining the perturbation signals that are of moderate amplitude by plotting a real and imaginary part of a higher order harmonic versus the perturbation amplitude raised to a power the same as the order of the harmonic;

(f) when the plot is not substantially linear, changing the perturbation amplitude and repeating step (e);

(g) with the computer, when the plot is substantially linear, deriving the amplitude-independent harmonic structure comprising at least one higher order harmonic greater than one using response signals sampled when the perturbation signals are of moderate amplitude; and (h) with the computer, identifying from a library of standard harmonic data, a model that matches the harmonic structure to characterize a rate-limiting electrochemical process of the electrochemical system.

15. The method of claim 14, wherein the finite power series is less than 10 terms.

16. The method of claim 14, wherein the finite power series is less than 4 terms.

17. The method of claim 14, wherein the finite power series is greater than 1 term.

* * * * *